US006326364B1

(12) United States Patent
Lin et al.

(10) Patent No.: US 6,326,364 B1
(45) Date of Patent: Dec. 4, 2001

(54) USE OF 5-AMINOSALICYLATES AS ANTIMICROBIAL AGENTS

(75) Inventors: Henry C. Lin, Manhattan Beach; Mark Pimentel, Los Angeles, both of CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 09/246,645

(22) Filed: Feb. 8, 1999

(51) Int. Cl.$^7$ ..................................................... A61K 31/60

(52) U.S. Cl. ......................... 514/154; 514/159; 514/161; 514/166

(58) Field of Search .................................. 514/154, 159, 514/161, 166

(56) References Cited

U.S. PATENT DOCUMENTS

| | | | |
|---|---|---|---|
| Re. 033,239 | 6/1990 | Halskov . | |
| 3,412,090 | 11/1968 | Knusli et al. | 260/242 |
| 4,657,900 | 4/1987 | Powell et al. | 514/166 |
| 4,863,744 | 9/1989 | Urquhart et al. | 424/484 |
| 4,960,765 | 10/1990 | Halskov | 514/166 |
| 5,010,069 | 4/1991 | Bottom et al. | 514/166 |
| 5,013,727 | 5/1991 | Halskov | 514/166 |
| 5,082,651 | 1/1992 | Healey et al. . | |
| 5,120,306 | 6/1992 | Gosselin | 604/51 |
| 5,352,681 | 10/1994 | Wittebrood et al. | 514/166 |
| 5,519,014 | 5/1996 | Borody | 514/159 |
| 5,731,302 | 3/1998 | Farolfi et al. | 514/166 |

FOREIGN PATENT DOCUMENTS

| | | |
|---|---|---|
| 0 468 555 A1 | 1/1992 | (EP) . |
| 0 882 461 A2 | 6/1998 | (EP) . |
| 1.605.124 | 9/1973 | (FR) . |
| WO 92/06690 A1 | 4/1992 | (WO) . |
| WO 94/28911 A1 | 12/1994 | (WO) . |
| WO 97/28795 A1 | 8/1997 | (WO) . |
| WO 98/07458 A1 | 2/1998 | (WO) . |

OTHER PUBLICATIONS

International Search Repor re PCT/US00/02802, International Date: Apr. 2, 2000.
XP–002154689, Takeda Chem. Ind. Ltd., Stabilized Drug Animal.
XP–002154690, Nippon Paint Co. Ltd., Composition.
XP–000972467, Sandberg–Gertzen, H. et al., In Vitro Effects of Sulphasalazine, Azoidsal Sodium, and Their Metabolites on Clostridium difficile and Some Other Faecal Bacteria, Scand J Gastroenterol 20:607–612 (1985).
XP–000972469, Triadafilopoulos, George et al., Comparative Study of Clostridum difficile Toxin A and Cholera Toxin in Rabbit Ileum, *Gastroenterology*, vol. 97., pp. 1186–1192 (1989).
Allgayer, H; Sulfasalazine and 5–ASA Compounds; *Gastroenterol Clin North Am*; vol. 21(3):643–658; Sep. 1992.
Al–Sheikhly, et al; The Interaction of Clostridium Perfringens and Its Toxin in the Production of Necrotic Enteritis of Chickens; *Avian Dis*; vol. 21(2):256–63; Apr.–Jun. 1977 (ABSTRACT ONLY).
Batta, et al; Synthesis and Intestinal Metabolism of Ursodeoxycholic Acid Conjugate with an Antiinflammatory Agent, 5–Aminosalicylic Acid; *J Lipid Research*; vol. 39:1641–46; 1998.
Bell, et al; Safety of Topical 5–Aminosalicylic Acid in Pregnancy; *Am J Gastroenterol*; vol. 92(12): 2201–2; Dec. 1997 (ABSTRACT ONLY).
Botoman, et al; Management of Inflammatory Bowel Disease; *Am Fam Phys*; vol. 57(1):57–68; Jan. 1, 1998.
Brett, et al; Detection of Clostridium Perfringens and Its Enterotoxin in Cases of Sporadic Diarrhoea; *J Clin Pathol*; vol. 45(7):609–11; Jul. 1992 (ABSTRACT ONLY).
Brimblecombe, R; Mesalazine: A Global Safety Evaluation; *Scand J. Gastroenterol Suppl*; vol. 172:66; 1990 (ABSTRACT ONLY).
Brogden, et al; Mesalazine: A Review of Its Pharmacodynamic and Pharmacokinetic Properties, and Therapeutic Potential in Chronic Inflammatory Bowel Disease; *Drugs*; 38(4):500–23; 1989.
Brown, et al; Colonic Spread of Three Rectally Administered Mesalazine (Pentasa) Dosage Forms in Healthy Volunteers as Assessed by Gamma Scintigraphy; *Aliment Pharmacol Ther*; vol. 11(4):685–91; Aug. 1997 (ABSTRACT ONLY).

(List continued on next page.)

*Primary Examiner*—Kevin E. Weddington
(74) *Attorney, Agent, or Firm*—Sidley Austin Brown & Wood

(57) ABSTRACT

A method of inhibiting the growth of a bacterial species in a human or non-human vertebrate employs the antimicrobial (i.e., antibiotic) properties of 5-aminosalicylates. These antimicrobial properties are also employed in an antimicrobial method of inhibiting the growth of a bacterial species in a foodstuff and in foodstuffs containing a 5-aminosalicylate compound. Pharmaceutical compositions, foodstuffs, food containers, food-handling implements, cleansers, polishes, paints, sprays, soaps, or detergents comprise 5-aminosalicylate compounds, such as mesalamine, sulphasalazine, olsalazine, ipsalazine, salicylazobenzoic acid, balsalazide, or conjugated bile acids, including ursodeoxycholic acid-5-aminosalicylic acid. The present pharmaceutical compositions can be formulated for ingestive, colonic, or topical non-systemic delivery systems or for any systemic delivery systems. Formulation can be for human or veterinary administration. Using the method and pharmaceutical preparations the growth of bacterial species, such as *Clostridium perfringens, Clostridium difficile, Clostridium botulinum*, and *Clostridium tetani* can be inhibited.

84 Claims, No Drawings-

OTHER PUBLICATIONS

Bueschel, et al; Enterotoxigenic *Clostridium Perfringens* Type A Necrotic Enteritis in a Foal; *J Am Vet Med Assoc*; vol. 213(9):1305–7, 1280; Nov. 1, 1998 (ABSTRACT ONLY).

Bruckstein, AH; New Salicylate Therapies for Ulcerative Colitis; *Postgrad Med*; vol. 88(3):79–82, 89; Sep. 1, 1990 (ABSTRACT ONLY).

Clarke, et al; *Enteritis Necroticans* with Midgup Necrosis Caused by *Clostridium Perfringens*; *Arch Surg*; vol. 129(5):557–60; May 1994 (ABSTRACT ONLY).

Claussen, D; Asacol (Mesalamine); *Gastroenterol Nurs*; vol. 15(1):33–4; Aug. 1992 (ABSTRACT ONLY).

Cleary, RK; Clostridium Difficite–Associated Diarrhea and Colitis: Clinical Manifestations, Diagnosis, and Treatment; *Dis Colon Rectum*; vol. 41(11):1435–49; Nov. 1998 (ABSTRACT ONLY).

Cohen, et al; Isolation of a Toxin B–Deficient Mutant Strain of Clostridium Difficile in a Case of Recurrent C. Difficile–Associated Diarrhea; *Clin Infect Dis*; vol. 26(2); 410–2, Feb. 1998 (ABSTRACT ONLY).

Cunha, BA; Nosocomila Diarrhea; *Crit Care Clin*; vol. 14(2):329–38; Apr. 1998 (ABSTRACT ONLY).

Diav–Citrin, et al; The Safety of Mesalamine in Human Pregnancy: A Prospective Controlled Cohort Study; *Gastroenterology*; vol. 114(1):23–8; Jan. 1998 (ABSTRACT ONLY).

Fockens, et al; Comparison of the Efficacy & Safety of 1.5 Compared with 3.0 g Oral Slow–Release Mesalazine (Pentasa) in the Maintenance Treatment of Ulcerative Colitis, Dutch Pentasa Study Group: *Eur J Gastroenterol Hepatol*; vol. 7(11):1025–30; Nov. 1995 (ABSTRACT ONLY).

Gionchetti, et al; Retrograde Colonic Spread of a New Mesalazine Rectal Enema in Patients with Distal Ulcerative Colitis, *Aliment Pharmacol Ther*, vol. 11(4):679–84; Aug. 1997 (ABSTRACT ONLY).

Gionchetti, et al; Comparison of Mesalazine Suppositories in Proctitis and Distal Proctosigmoiditis, *Aliment Pharmacol Ther*, vol. 11(6):1053–7; Dec. 1997 (ABSTRACT ONLY).

Goncalves, et al; Antioxidant Activity of 5–Aminosalicylic Acid Against Peroxidation of Phosphatidylcholine Liposomes in the Presence of Alpha–Tocopherol: A Synergistic Interaction?; *Free Radic Res*; vol. 29(1):53–66; Jul. 1998 (ABSTRACT ONLY).

Green, et al; Maintenance of Remission of Ulcerative Colitis: A Comparison Between Balsalazide 3 g Daily and Mesalazine 1.2 g Daily Over 12 Months, ABACUS Investigator Group, *Aliment Pharmacol Ther*, vol. 12(12):1207–16; Dec. 1998 (ABSTRACT ONLY).

Green, et al; Balsalazide in More Effective and Better Tolerated than Mesalazine in the Treatment of Acute Ulcerative Colitis. ABACUS Investigator Group, *Gastroenterology*, vol. 114(1):15–22; Jan. 1998 (ABSTRACT ONLY).

Greenfield, et al; Review Article: The Mode of Action of the Aminosalicylates in Inflammatory Bowel Disease; *Aliment Pharmol Ther*; vol. 7(4):369–83; Aug. 1993 (ABSTRACT ONLY).

Griffin, et al; Conventional Drug Therapy in Inflammatory Bowel Disease; *Gastroenterol Clin North Am*; vol. 24(3):509–521; Sep. 1995.

Hanauer, et al; Medical Therapy of Inflammatory Bowel Disease; *Med Clinics North Am*; vol. 78(5):1413–26; Nov. 1994.

Hanauer, et al; Risk–Benefit Assessment of Drugs Used in the Treatment of Inflammatory Bowel Disease; *Drug Saf*; vol. 6(3):192–219; May–Jun. 1991 (ABSTRACT ONLY).

Hanauer, et al; The Role of Mesalazine in Crohn's Disease; *Scan J Gastroenterol*; vol. 25 (Supple 172):56–59; 1990.

Job, et al; Drug–Induced Clostridium Difficile–Associated Disease; *Drug Saf*; vol. 17(1):37–46; Jul. 1997 (ABSTRACT ONLY).

Kang, et al; Salicylate Inhibits Fimbriae Mediated HEp–2 Cell Adherence of and Haemagglutination by Enteroaggregative *Escherichia coli; FEMS Microbiol Lett*; vol. 166(2):257–65; Sep. 15, 1998 (ABSTRACT ONLY).

Kruis, et al; Double–Blind Comparison of an Oral *Escherichia Coli* Preparation and Mesalazine in Maintaining Remission of Ulcerative Colitis; *Aliment Pharmacol Ther*; vol. 11(5):853–8; Oct. 1997 (ABSTRACT ONLY).

Kruis, et al; Olsalazine versus Mesalazine in the Treatment of Mild to Moderate Ulcerative Colitis; *Aliment Pharmacol Ther*; vol. 12(8):707–15; Aug. 1998 (ABSTRACT ONLY).

Marteau, et al; Use of Mesalazine Slow Release Suppositories 1 g Three Times per Week to Maintain Remission of Ulcerative Proctitis: A Randomised Double Blind Placebo Controlled Multicentre Study; *Gut* vol. 42(2):195–9; Feb. 1998 (ABSTRACT ONLY).

Marteau, et al; Foetal Outcome in Women with Inflammatory Bowel Disease Treated During Pregnancy with Oral Mesalazine Microgranules; *Aliment Pharmacol Ther*; vol. 12(11):1101–8; Nov. 1998 (ABSTRACT ONLY).

Martin, Fl; Oral 5–Aminosalicyclic Acid Preparations in Treatment of Inflammatory Bowel Disease, An Update; *Digestive Diseases & Sciences*; vol. 32(12):57S–63S; Dec. 1987 Supplement.

Mpamugo, et al; Enterotoxigenic *Clostridium Perfringens* as a Cause of Sporadic Cases of Diarrhea; *J Med Microbiol*; vol. 43(6):442–5; Dec. 1995; (ABSTRACT ONLY).

Mulder, et al; Drug Therapy: Dose–Response Relationship of Oral Mesalazine in Inflammatory Bowel Disease; *Mediators Inflamm*; vol. 7(3):135–6; 1998; (ABSTRACT ONLY).

Nakajima et al; Adverse Effects of Sulfasalazine and Treatment of Ulcerative Colitis with Mesalazine; *J. Gastroenterol*; vol. 30 Suppl 8:115–7; Nov. 1995; (ABSTRACT ONLY).

Osterwald, HP; Pharmaceutic Development: Mesalazine; *Scand J Gastroenterol Suppl*; vol. 172:43–6; 1990; (ABSTRACT ONLY).

Otten, et al; Colonic Spread of 5–ASA Enemas in Healthy Individuals with a Comparison of Their Physical and Chemical Characteristics; *Aliment Pharmacol Ther*; vol. 11(4):693–7; Aug. 1997; (ABSTRACT ONLY).

Pearson, et al; Hemorrhagic Enteritis Caused by *Clostridium Perfringens* Type C in a Foal; *J Am Vet Med Assoc*; vol. 188(11)1309–10; Jun. 1986; (ABSTRACT ONLY).

Peppercorn, MA; Advances in Drug Therapy for Inflammatory Bowel Disease; *Annals Intern Med*; vol. 112(1):50–60; 1990.

Pollock et al; Outbreak of *Clostridium Perfringens* Food Poisoning; *J Hosp Infect*; vol. 17(3):179–86; Mar. 1991 (ABSTRACT ONLY).

Pothoulakis, et al; Clostridium Difficile Colitis and Diarrhea; *Gastroenterol Clin North Am*; vol. 22(3):623–37; Sep. 1993; (ABSTRACT ONLY).

Rasmussen, SN; Bioavailability of Controlled Release Mesalazine (5–ASA Preparations); *J Gastroenterol*; vol. 30 Suppl 8:112–4; Nov. 1995; (ABSTRACT ONLY).

Rijk et al; Disposition of Mesalazine from Mesalazine–Delivering Drugs in Patients with Inflammatory Bowel Disease with and without Diarrhoea; *Scand J Gastroenterol*; vol. 27(10):863–8; Oct. 1992 (ABSTRACT ONLY).

Small, et al; Chemistry, Pharmacology, Pharmacokinetic, and Clinical Applications of Mesalamine for the Treatment of Inflammatory Bowel Disease; *Pharmacothereapy* vol. 14(4):385–98; Jul.–Aug. 1994 (ABSTRACT ONLY).

Stotland, et al; Medical Therapies for Inflammatory Bowel Disease; *Hosp Pract (Off Ed)*; vol. 33(5):141–4, 149–51, 156 passim; May 15, 1998 (ABSTRACT ONLY).

Surawicz, CM; Clostridium Difficile Disease: Diagnosis and Treatment; *Gastroenterologist*; vol. 6(1):60–6; Mar. 1998 (ABSTRACT ONLY).

Thomson, AB; Review Article: New Developments in the Use of 5–Aminosalicylic Acid in Patients with Inflammatory Bowel Disease; *Aliment Pharmacol Ther*; vol. 5(5):449–70; Oct. 1991 (ABSTRACT ONLY).

Thompson, EG; Irritable Bowel Syndrome: Pathogenesis and Management; *Lancet*; vol. 341:1569–72; Jun. 19, 1993.

van Loon, et al; Clostridium Perfringens Type C in Bloody and Watery Diarrhea in Bangladesh; *Trop Geogr Med*; vol. 42(2):123–7; Apr. 1990 (ABSTRACT ONLY).

Wada, et al; Nosocomial Diarrhoea in the Elderly Due to Enterotoxigenic *Clostridium Perfringens; Microbiol Immunol*; vol. 40(10):767–71; 1996 (ABSTRACT ONLY).

Wadworth, et al; Olsalazine. A Review of its Pharmacodynamic and Pharmacokinetic Properties, and Therapeutic Potential in Inflammatory Bowel Disease; *Drugs*; vol. 41(4):647–64; Apr. 1991 (ABSTRACT ONLY).

Watson et al; Pig–Bel but No Pig: *Enterities Necroticans* Acquired in Australia; *Med J Aust*; vol. 155(1):47–50; Jul. 1, 1991 (ABSTRACT ONLY).

Allgayer, H; Sulfasalazine and 5–ASA Compounds; *Gastroenterol Clin North Am*; vol. 21(3):643–658; Sep. 1992.

Al–Sheikhly, et al; The Interaction of *Costridium Perfringens* and Its Toxins in the Production of *Necrotic Enteritis* of Chickens; *Avian Dis*; vol. 21(2):256–63; Apr.–Jun. 1977 (ABSTRACT ONLY).

Batta, et al; Synthesis and Intestinal Metabolism of Ursodeoxycholic Acid Conjugate with an Antiinflammatory Agent, 5–Aminosalicyclic Acid; *J Lipid Research*; vol. 39:1641–46; 1998.

Bell, et al; Safety of Topical 5–Aminosalicylic Acid in Pregnancy; *Am J Gastroenterol*; vol. 92(12): 2201–2; Dec. 1997 (ABSTRACT ONLY).

Botoman, et al; Management of Inflammatory Bowel Disease; *Am Fam Phys*; vol. 57(1):57–68; Jan. 1, 1998.

Brett, et al; Detection of *Clostridium Perfringens* and Its Exterotoxin in Cases of Sporadic Diarrhoea; *J Clin Pathol*; vol. 45(7):609–11; Jul. 1992 (ABSTRACT ONLY).

Brimblecombe, R; Mesalazine: A Global Safety Evaluation; *Scand J. Gastroenterol Suppl*; vol. 172:66; 1990 (ABSTRACT ONLY).

Brogden, et al; Mesalazine: A Review of Its Pharmacodynamic and Pharmacokinetic Properties, and Therapeutic Potential in Chronic Inflammatory Bowel Disease; *Drugs*; 38(4):500–23; 1989.

Brown, et al; Colonic Spread of Three Rectally Administered Mesalazine (Pentasa) Dosage Forms in Healthy Volunteers as Assessed by Gamma Scintigraphy; *Aliment Pharmacol Ther*; vol. 11(4):685–91; Aug. 1997 (ABSTRACT ONLY).

Bueschel, et al; Enterotoxigenic *Clostridium Perfringens* Type A Necrotic Enteritis in a Foal; *J Am Vet Med Assox*; vol. 213(9):1305–7, 1280; Nov. 1, 1998 (ABSTRACT ONLY).

Bruckstein, AH; New Salicylate Therapies for Ulcerative Colitis; *Postgrad Med*; vol. 88(3):79–82, 89; Sep. 1, 1990 (ABSTRACT ONLY).

Clarke, et al; *Enteritis Necroticans* with Midgut Necrosis Caused by *Clostridium Perfringens*; *Arch Surg*; vol. 129(5):557–60; May 1994 (ABSTRACT ONLY).

Claussen, D; Asacol (Mesalamine); *Gastroenterol Nurs*; vol. 15(1):33–4; Aug. 1992 (ABSTRACT ONLY).

Cleary, RK; Clostridium Difficile–Associated Diarrhea and Colitis: Clinical Manifestations, Diagnosis, and Treatment; *Dis Colon Rectum*; vol. 41(11):1435–49; Nov. 1998 (ABSTRACT ONLY).

Cohen, et al; Isolation of a Toxin B–Deficient Mutant Strain of *Clostridium Difficile* in a Case of Recurrent *C. Difficule*–Associated Diarrhea; *Clin Infect Dis*; vol. 26(2); 410–2, Feb. 1998 (ABSTRACT ONLY).

Cunha, BA; Nosocomial Diarrhea; *Crit Care Clin*; vol. 14(2):329–38; Apr. 1998 (ABSTRACT ONLY).

Diav–Citrin, et al; The Safety of Mesalamine in Human Pregnancy: A Prospective Controlled Cohort Study; *Gastroenterology*; vol. 114(1):23–8; Jan. 1998 (ABSTRACT ONLY).

Fockens, et al; Comparison of the Efficacy & Safety of 1.5 Compared with 3.0 g Oral Show–Release Mesalazine (Pentasa) in the Maintenance Treatment of Ulcerative Colitis. Dutch Pentasa Study Group; *Eur J Gastroenterol Hepatol*; vol. 7(11):1025–30; Nov. 1995 (ABSTRACT ONLY).

Gionchetti, et al; Retrograde Colonic Spread of a New Mesalazine Rectal Enema in Patients with Distal Ulcerative Colitis, *Aliment Pharamacol Ther*, vol. 11(4):679–84; Aug. 1997 (ABSTRACT ONLY).

Gionchetti, et al; Comparison of Mesalazine Suppositories in Proctitis and Distal Proctosigmoiditis, *Aliment Pharmacol Ther*, vol. 11(6):1053–7; Dec. 1997 (ABSTRACT ONLY).

Goncalves, et al; Antioxidant Activity of 5–Aminosalicylic Acid Against Peroxidation of Phosphatidylcholine Liposomes in the Presence of Alpha–Tocopherol: A Synergistic Interaction?; *Free Radic Res*; vol. 29(1):53–66; Jul. 1998 (ABSTRACT ONLY).

Green, et al; Maintenance of Remission of Ulcerative Colitis: A Comparison Between Balsalazide 3 g Daily and Mesalazine 1.2 g Daily Over 12 Months. ABACUS Investigator Group, *Aliment Pharmacol Ther*, vol. 12(12):1207–16; Dec. 1998 (ABSTRACT ONLY).

Green, et al; Balsalazide is More Effective and Better Tolerated than Mesalazine in the Treatment of Acute Ulcerative Colitis. ABACUS Investigatot Group, *Gastroenterology*, vol. 114(1):15–22; Jan. 1998 (ABSTRACT ONLY).

Greenfield, et al; Review Article: The Mode of Action of the Aminosalicylates in Inflammatory Bowel Disease; *Aliment Pharmol Ther*; vol. 7(4):369–83; Aug. 1993 (ABSTRACT ONLY).

Griffin, et al; Conventional Drug Therapy in Inflammatory Bowel Disease; *Gastroenterol Clin North Am*; vol. 24(3):509–521; Sep. 1995.

Hanauer, et al; Medical Therapy of Inflammatory Bowel Disease; *Med Clinics North Am*; vol. 78(6):1413–26; Nov. 1994.

Hanauer, et al; Risk–Benefit Assessment of Drugs Used in the Treatment of Inflammatory Bowel Disease; *Drug Saf*; vol. 6(3):192–219; May–Jun. 1991 (ABSTRACT ONLY).

Hanauer, et al; The Role of Mesalazine in Crohn's Disease; *Scan J Gastroenterol*; vol. 25 (Supple 172):56–59, 1990.

Job, et al; Drug–Induced *Clostridium Difficile*–Associated Disease; *Drug Saf*; vol. 17(1):37–46; Jul. 1997 (ABSTRACT ONLY).

Kang, et al; Salicylate Inhibits Fimbriae Mediated HEp–2 Cell Adherence of and Haemagglutination by Enteroaggregative *Escherichia coli*; *FEMS Microbiol Lett*; vol. 166(2):257–65; Sep. 15, 1998 (ABSTRACT ONLY).

Kruis, et al; Double–Blind Comparison of an Oral *Escherichia Coli* Preparation and Mesalazine in Maintaining Remission of Ulcerative Colitis; *Aliment Pharmacol Ther*; vol. 11(5):853–8; Oct. 1997 (ABSTRACT ONLY).

Kruis, et al; Olsalazine versus Mesalazine in the Treatment of Mild to Moderate Ulcerative Colitis; *Aliment Pharmacol Ther*; vol. 12(8):707–15; Aug. 1998 (ABSTRACT ONLY).

Marteau, et al; Use of Mesalazine Slow Release Suppositories 1 g Three Times per Week to Maintain Remission of Ulcerative Proctitis: A Randomised Double Blind Placebo Controlled Multicentre Study; *Gut* vol. 42(2):195–9; Feb. 1998 (ABSTRACT ONLY).

Marteau, et al; Foetal Outcome in Women with Inflammatory Bowel Disease Treated During Pregnancy with Oral Mesalazine Microgranules; *Aliment Pharmacol Ther*; vol. 12(11):1101–8; Nov. 1998 (ABSTRACT ONLY).

Martin, FI; Oral 5–Aminosalicylic Acid Preparations in Treatment of Inflammatory Bowel Disease, An Update; *Digestive Diseases & Sciences*; vol. 32(12):57S–63S; Dec. 1987 Supplement.

Mpamugo, et al; Enterotoxigenic *Clostridium Perfringens* as A Cause of Sporadic Cases of Diarrhoea; *J Med Microbiol*; vol. 43(6):442–5; Dec. 1995; (ABSTRACT ONLY).

Mulder, et al; Drug Therapy: Dose–Response Relationship of Oral Mesalazine in Inflammatory Bowel Disease; *Mediators Inflamm*; vol. 7(3):135–6; 1998; (ABSTRACT ONLY).

Nakajima, et al; Adverse Effects of Sulfasalazine and Treatment of Ulcerative Colitis with Mesalazine; *J Gastroenterol*; vol. 30 Suppl 8:115–7; Nov. 1995; (ABSTRACT ONLY).

Osterwald, HP; Pharmaceutic Development; Mesalazine; *Scand J Gastroenterol Suppl*; vol. 172:43–6; 1990; (ABSTRACT ONLY).

Otten, et al; Colonic Spread of 5–ASA Enemas in Healthy Individuals, with a Comparison of Their Physical and Chemical Characteristics; *Aliment Pharmacol Ther*; vol. 11(4):693–7; Aug. 1997; (ABSTRACT ONLY).

Pearson, et al; The Anti–Oxidant Properties of 5–Aminosalicylic Acid; *Free Radic Biol Med*; vol. 21(3):367–73; 1996 (ABSTRACT ONLY).

Pearson, et al; Hemorrhagic Enteritis Caused by *Clostridium Perfringens* Type C in a Foal; *J Am Vet Med Assoc*; vol. 188(11)1309–10; Jun. 1986; (ABSTRACT ONLY).

Peppercom, MA; Advances in Drug Therapy for Inflammatory Bowel Disease; *Annals Intern Med*; vol. 112(1):50–60; 1990.

Pollock et al; Outbreak of *Clostridium Perfringens* Food Poisoning; *J Hosp Infect*; vol. 17(3):179–86; Mar. 1991 (ABSTRACT ONLY).

Pothoulakis, et al; *Clostridium Difficile* Colitis and Diarrhea; *Gastroenterol Clin North Am*; vol. 22(3):623–37; Sep. 1993; (ABSTRACT ONLY).

Rasmussen, SN; Bioavailability of Controlled Release Mesalazine (5–ASA Preparations); *J Gastroenterol*; vol. 30 Suppl 8:112–4; Nov. 1995; (ABSTRACT ONLY).

Rijk et al; Disposition of Mesalazine from Mesalazine–Delivering Drugs in Patients with Inflammatory Bowel Disease with and without Diarrhoea; *Scand J Gastroenterol*; vol. 27(10):863–8; Oct. 1992 (ABSTRACT ONLY).

Small, et al; Chemistry, Pharmacology, Pharmacokinetic, and Clinical Applications of Mesalamine for the Treatment of Inflammatory Bowel Disease; *Pharmacothereapy* vol. 14(4):385–98; Jul.–Aug. 1994 (ABSTRACT ONLY).

Stotland, et al; Medical Therapies for Inflammatory Bowel Disease; *Hosp Pract (Off Ed)*; vol. 33(5):141–4, 149–51, 156 passim; May 15, 1998 (ABSTRACT ONLY).

Surawicz, CM; *Clostridium Difficile* Disease: Diagnosis and Treatment; *Gastroenterologist*; vol. 6(1):60–6; Mar. 1998 (ABSTRACT ONLY).

Thomson, AB; Review Article: New Development in the Use of 5–Aminosalicylic Acid in Patients with Inflammatory Bowel Disease; *Aliment Pharmacol Ther*; vol. 5(5):449–70; Oct. 1991 (ABSTRACT ONLY).

Thompson, EG; Irritable Bowel Syndrome: Pathogenesis and Management; *Lancet*; vol. 341:1569–72; Jun. 19, 1993.

van Loon, et al; *Clostridium Perfringens* Type C in Bloody and Watery Diarrhea in Bangladesh; *Trop Geogr Med*; vol. 42(2):123–7; Apr. 1990 (ABSTRACT ONLY).

Wada, et al; Nosocomial Diarrhoea in the Elderly Due to Enterotoxigenic *Clostridium Perfringens*; *Microbiol Immunol*; vol. 40(10):767–71; 1996 (ABSTRACT ONLY).

Wadworth, et al; Olsalazine. A Review of its Pharmacodynamic and Pharmacokinetic Properties, and Therapeutic Potential in Inflammatory Bowel Disease; *Drugs*; vol. 41(4):647–64; Apr. 1991 (ABSTRACT ONLY).

Watson, et al; Pig–Bel but No Pig: Enterities Necroticans Acquired in Australia; *Med J Aust*; vol. 155(1):47–50; Jul. 1, 1991 (ABSTRACT ONLY).

USE OF 5-AMINOSALICYLATES AS ANTIMICROBIAL AGENTS

BACKGROUND OF THE INVENTION

Throughout this application various publications are referenced within parentheses. The disclosures of these publications in their entireties are hereby incorporated by reference in this application in order to more fully describe the state of the art to which this invention pertains.

1. The Field of the Invention

This invention relates to the medical arts. In particular, it relates to a method of inhibiting bacterial growth in the gastrointestinal tract of a human or non-human vertebrate by using an antimicrobial agent.

2. Discussion of the Related Art

Antimicrobial or antibiotic agents are used in the treatment of bacterial infections, especially of the gastrointestinal tract. Gastrointestinal infections affect millions of people world-wide, especially children, and pose an increasing health hazard in hospital settings.

Of course, bacteria inhabit healthy intestines to the benefit of their human and animal hosts. Anaerobic bacteria, including the *Bacteroides fragilis* group and Clostridium species are common members of the intestinal microflora of healthy individuals, and non-toxigenic strains can be transmitted without causing disease symptoms. (B. A. Cunha, *Nosocomial diarrhea*, Crit. Care Clin. 14(2):329–38 [1998]; H. Kato et al., Application of typing by pulsed-yield gel electrophoresis to the study of *Clostridium difficile* in a neonatal intensive care unit, J. Clin. Microbiol. 32(9):2067–70 [1997]; V. O. Rotimi and B. I. Duerden, Bacteroides species in the normal neonatal faecal flora, J. Hyg. [Lond.] 87(2):299–304 [1981]; B. I. Duerden, The isolation and identification of Bacteroides spp. From the normal human faecalflora, J. Med. Microbiol. 13(1):69–78 [1980]; S. S. Long and R. M. Swenson, Development of anaerobic flora in healthy newborn infants, J. Pediatr. 91(2):298–301 [1977]). Other pathogenic bacterial strains have an adverse effect on their hosts.

For example, enterotoxigenic strains of *Bacteroides fragilis* are associated with diarrhea in humans. (S. K. Niyogi et al., Association of enterotoxigenic *Bacteroides fragilis* with childhood diarrhoea, Indian J. Med. Res. 105:167–69 [1997]; R. B. Sack et al., Enteroloxigenic *Bacteroides fragilis*: epidemiologic studies of its role as a human diarrhoeal pathogen, J. Diarrhoeal Dis. Res. 10(1):4–9 [1992]). And patients with Crohn's disease were reported to have higher numbers of *B. fragilis* group bacteria in their intestines than healthy controls. (J. G. Ruseler-van Embden and H.C. Both-patoir, Anaerobic gram-negative faecal flora in patients with Crohn's disease and healthy subjects, Antonie van Leeuwenhoek 49(2):125–32 [1983]).

More prominent agents of gastrointestinal disease than Bacteroides, are the Clostridium species, especially *C. difficile* and *C. perfringens*. Clostridium species are gram-positive, spore-forming anaerobes; some strains that colonize the human intestines can, under certain circumstances, release potent protein exotoxins that induce inflammation of the intestinal mucosa. (M. L. Job and N. F. Jacobs, Jr., Drug-induced *Clostridium difficile*-associated disease, Drug Saf. 17(1):37–46 [1997]). For example, antibiotics and other chemotherapeutic agents can induce the expression of Toxins A and B from *Clostridium difficile*. (B. A. Cunha [1998]). Agents known to have a high potential to induce *C. difficile*-associated disease are aminopenicillins, cephalosporins and clindamycin. (M. L. Job and N. F. Jacobs, Jr., Drug-induced *Clostridium difficile*-associated disease, Drug. Saf. 17(1):37–46 [1997]; Y. Hutin et al., Prevalence of and risk factors for *Clostridium difficile* colonization at admission to an infectious diseases ward, Clin. Infect. Dis. 24(5):920–24 [1997]; C. D. Settle and M. H. Wilcox [1996]).

In developed countries, the great majority of cases of *C. difficile* infection are hospital-acquired, and the number of nosocomial clostridial infections is reported to be rising. (C. D. Settle and M. H. Wilcox, Review article: antibiotic-induced *Clostridium difficile* infection, Aliment. Pharmacol. Ther. 10(6):835–41[1996]; J. S. Brazier, The epidemiology and typing of *Clostridium difficile*, J. Antimicrob. Chemother. 41 Suppl. C:47–57 [1998]; S. Tabaqchali and M. Wilks, Epidemiological aspects of infections caused by *Bacteroides fragilis* and *Clostridium difficile*, Eur. J. Clin. Microbiol. Infect. Dis. 11(11): 1049–57 [1992]; C. R. Clabots et al., Acquisition of *Clostridium difficile* by hospitalized patients: evidence for colonized new admissions as a source of infection, J. Infect. Dis. 166(3):561–67 [1992]).

A nosocomial pleural infection with *C. difficile*, following surgical insertion of a chest drain has also been reported (A. J. Simpson et al., Nosocomial empyema caused by *Clostridium difficile*, J. Clin. Pathol. 49(2):172–73 [1996]), but intestinal infections are the greatest problem.

Nosocomial diarrhea due to gastrointestinal infection with *C. difficile* has become a major health care problem, causing 20–30% of all nosocomial diarrheas and affecting up to 8% of hospitalized patients. (L. R. Peterson and P. J. Kelly, The role of the clinical microbiology laboratory in the management of *Clostridia difficile*-associated diarrhea, Infect. Dis. Clin. North Am. 7(2):277–93 [1993]). *Clostridium difficile* is considered to be the premier cause of diarrhea among hospitalized patients. (M. Delmee et al., Treatment of *Clostridium difficile* colitis. Summary of a round table held in Brussels on Mar. 3, 1994, Acta Clin. Belg. 50(2):114–116 [1995]).

An infection of *C. difficile* can add an average of three weeks to a patient's hospital stay. (C. D. Settle and M. H. Wilcox [1996]). Symptoms may include, diarrhea, self-limited colitis, toxic megacolon or potentially lethal fulminant pseudomembranous colitis. Intestinal infection with *C. difficile* has also been linked to reactive arthritis. (I. H. Kocar et al., Clostridium infection in patients with reactive arthritis of undetermined etiology, Scand. J. Rheumatol. 27(5):357–62 [1998]; R. K. Cleary, *Clostridium difficile*-associated diarrhea and colitis: clinical manifestations, diagnosis, and treatment, Dis. Colon. Rectum 41(11):1435–49 [1998]). Bacteraemia and subsequent sepsis is another possible complication of intestinal infection by *C. difficile*. (P. Naaber et al., Bacterial translocation, intestinal microflora and morphological changes of intestinal mucosa in experimental models of *Clostridium difficile* infection, J. Med. Microbiol. 47(7):591–98 [1998]; R. J. Feldman et al., Bacteremia due to *Clostridium difficile*: case report and review of extraintestinal *C. Difficile* infections, Clin. Infect. Dis. 20(6):1560–62 [1995]). In at least one nosocomial outbreak, 17 patients died from *C. difficile* infection. (C. D. Settle and M. H. Wilcox [1996]). *Clostridium difficile* intestinal infections in children, unassociated with antibiotic use or hospital stays, can cause chronic diarrhea and failure to grow. (T. E. Liston, *Clostridium difficile* toxin associated with chronic diarrhea and failure to gain weight, Clin. Pediatr. (Phila.) 22(6):458–60 [1983]).

In developing countries, *C. difficile* is also thought to be a causal agent of wide-spread acute cliarrheal disease. (S. K.

Niyogi et al., Prevalence of *Clostridium difficile* in hospitalized patients with acute diarrhoea in Calcutta, J. Diarrhoeal Dis. Res. 9(1):16–19 [1991]; S. Q. Akhtar, Isolation of *Clostridium difficile* from diarrhoea patients in Bangladesh, J. Trop. Med. Hyg. 90(4):189–92 [1987]).

Enterotoxigenic strains of *C. perfringens* are linked with a significant number of cases of antibiotic-associated diarrhea, especially among elderly hospitalized patients, children, and infants. (A. Wada et al., Nosocomial diarrhoea in the elderly due to enterotoxigenic *Clostridium perfringens*, Microbiol. Immunol. 40(10):767–71 [1996]; M. M. Brett et al., Detection of *Clostridium perfringens* and its enterotoxin in cases of sporadic diarrhoea, J. Clin. Pathol. 45(7):609–11 [1992]; S. C. Samuel et al., An investigation into *Clostridium perfringens* enterotoxin-associated diarrhoea, J. Hosp. Infect. 18(3):219–30 [1991]; S. P. Boriello et al., Epidemiology of diarrhoea caused by enterotoxigenic *Clostridium perfringens*, J. Med. Microbiol. 20(3):363–72 [1985]; R. Willliams et al., Diarrhoea due to entertoxigenic *Clostridium perfringens*: clinical features and management of a cluster of 10 cases, Age Aging 14(5):296–302 [1985]). *Clostridium perfringens* has been implicated as a possible contributor to sudden infant death syndrome (SIDS) in susceptible infants. (R. R. Meer et al., Human disease associated with *Clostridium perfringens* enterotoxin, Rev. Environ. Contam. Toxicol. 150:75–94 [1997]).

*Clostridium perfringens* is well known as a causative agent of non-gastrointestinal gangrene, a special problem for many elderly and diabetic patients with poor blood circulation. But also in more extreme cases of gastrointestinal infection, *C. perfringens* can cause enteritis necroticans, a gangrene of the bowel resulting in necrosis, sepsis, and hemolysis, in humans and domesticated animals. (L. E. Clarke et al., Enteritis necroticans with midgut necrosis caused by *Clostridium perfringens*, Arch. Surg. 129(5):557–60 [1994]; D. Bueschel et al., Enterotoxigenic *Clostridium perfringens* type A necrotic enteritis in a foal, J. Am. Vet. Med. Assoc. 213(9):1305–07 [1998]; E. G. Pearson et al., Hemorrhagic enteritis caused by *Clostridium perfringens* type C in afoal, J. Am. Vet. Med. 188(11):1309–10 [1986]; F. Al-Sheikhy and R. B. Truscott, The interaction of *Clostridium perfringens* and its toxins in the production of necrotic enteritis of chickens, Avian Dis. 21(2):256–63 [1977]).

Although rare in developed countries, clostridial enteritis necroticans in humans is more common in some developing countries. (D. A. Watson et al., Pig-bel but no pig: enteritis necroticans acquired in Australia, Med. J. Aust. 155(1):47–50 [1991]). In New Guinea, enteritis necroticans, known locally as pigbel, has been a major cause of illness and death among children. (G. W. Lawrence et al., Impact of active immunisation against enteritis necroticans in Papua New Guinea, Lancet 336(8724): 1165–67 [1990]). *Clostridium perfringens* type C, the etiologic agent of enteritis necroticans, was also isolated from Bangladeshis with bloody or watery diarrheal illness. (F. P. van Loon et al., *Clostridium perfringens* type C in bloody and watery diarrhea in Bangladesh, Trop. Geogr. Med. 42(2):123–27 [1990]).

Entertoxigenic strains of *C. perfringens* have also been linked to nosocomial and non-nosocomial outbreaks of food poisoning, due to heat-resistant spores and a rapid growth rate in warm food. (A. M. Pollack and P. M. Whitty, Outbreak of *Clostridium perfringens* food poisoning, J. Hosp. Infect. 17(3):179–86 [1991]; M. Van Damme-Jongsten et al., Synthetic DNA probes for detection of enterotoxigenic *Clostridium perfringens* strains isolated from outbreaks of food poisoning, J. Clin. Microbiol. 28(1):131–33 [1990]).

Spores of *Clostridium botulinum* germinating in warm food can cause another form of food poisoning called botulism. Growing particularly in non-acidic foods lacking nitrites, and protected from oxygen, the vegetative cells of *C. botulinum* release an exotoxin that when consumed with the food is activated by trypsin in the stomach, and is absorbed intact by the blood stream. The exotoxin binds to nerve cells, preventing the release of the neurotransmitter acetylcholine. Resulting symptoms of botulism include blurred vision, difficulty in swallowing and speaking, and increasing muscular weakness, and usually nausea and vomiting. Death often results from paralysis of the muscles required for breathing. (R. Y. Stanier et al., *The Microbial World*, 5 th ed., Prentice Hall, Englewood Cliffs, N.J. pp.626–27 [1986]). *Clostridium botulinum* sometimes colonizes the intestines of infants and can cause infantile botulism, which can lead to respiratory paralysis and sudden infant death.

Botulism is a problem for the food packaging industry. Spores of *C. botulinum* may not be killed if canning is done at too low a temperature. High temperature autoclave treatment may be unsuitable for some foods Mayonnaise and other non-acidic foods are particularly prone to foster the growth of *C. botulinum*. Now with increasing health concerns about the use of nitrite as a food preservative, alternative antimicrobial agents are needed against the growth of *C. botulinum* and other food poisoning bacterial pathogens.

Antimicrobial agents with selective toxicity for a specific spectrum or range of pathogenic microorganisms are well known in the art. One class of antimicrobial agents is the antibiotics, which are compounds, synthesized and excreted by various microorganisms, that are selectively toxic to other microorganisms, specifically bacteria. In addition, some antibiotics can be artificially modified to produce antimicrobial agents that are more effective and/or more able to overcome antibiotic resistance.

The first line antibiotic treatment for diseases associated with gastrointestinal infections of Clostridium has been a 10-day course of metronidazole or vancomycin, which may be administered orally, intravenously, or rectally. (R. K. Cleary [1998]; C. P. Kelly and J. T. LaMont, *Clostridium difficile* infection, Annu. Rev. Med. 49:375–90 [1998]; C. M. Reinke and C. R. Messick, Update on *Clostridium difficile*-induced colitis, Part 2, Am. J. Hosp. Pharm. 51(15):1892–1901 [1994]).

Neither of these antibiotics has been completely satisfactory. While metronidazole (flagyl) is effective against obligate anaerobes (e.g., P. Muir et al., Breath hydrogen excretion by healthy cats after oral administration of oxytetracycline and metronidazole, Vet. Rec. 138:635–39 [1996]; B. Lembcke et al., Different actions of neomycin and metronidazole on breath hydrogen (H) exhalation, Z. Gastroenterol. 18(3):155–60 [1980]), it yields an unpleasant after-taste to many patients, even when delivered intravenously. Other common side effects of metronidazole are neuropathy and gastrointestinal distress. Also, metronidazole is a known reproductive toxicant affecting mammalian sperm cells. (R. E. Linder et al., Endpoints of spermatotoxicity in the rat after short duration exposures to fourteen reproductive toxicants, Reprod. Toxicol. 6(6):491–505 [1992]).

On the other hand, a course of vancomycin is prohibitively expensive (10–50 times more expensive than metronidazole), and there are concerns about the rapid development of vancomycin-resistance among pathogenic Clostridium, Enterococcus, Pediococcus, Citrobacter, Klebsiella, Enterobacter, and Staphylococcus species, because the plasmid-borne vancomycin resistance gene (VanR) is readily transmissible. (ASHP therapeutic position statement on the preferential use of metronidazole for the treatment of Clostridium difficile-associated disease, Am. J. Health Syst. Pharm. 55(13):1407–1 [1998]; S. H. Cohen et al., Isolation of a toxin B-deficient mutant strain of Clostridium difficile in a case of recurrent C. difficile-associated diarrhea, Clin. Infect. Dis. 26(2):1250 [1998]; C. Edlund et al., Effect of vancomycin on intestinal flora of patients who previously received antimicrobial therapy, Clin. Infect. Dis. 25(3):729–32 [1997]; C. A. O'Donovan et al., Enteric eradication of vancomycin-resistant Enterococcus faecium with oral bacitracin, Diagn. Microbiol. Infect. Dis. 18(2):105–09 [1994]; E. Yamaguchi et al., Colonization pattern of vancomvcin-resistant Enterococcus faecium, Am. J. Infect. Control 22(4):202–06 [1994]; C. P. Kelly and J. T. LaMont [1998]).

In addition, relapses of clostridial infections occur in about 5–42% of those treated with metronidazole or vancomycin and are believed to be caused by persistent endogenous clostridial spores, which are antibiotic resistant. (S. H. Cohen et al. [1998]; R. Fekety et al., Recurrent Clostridium difficile diarrhea: characteristics of and risk factors for patients enrolled in a prospective, randomized, double-blinded trial, Clin. Infect. Dis. 24(3):324–33 [1997]; S. Johnson et al., Treatment of asymptomatic Clostridium difficile carriers fecal excretors with vancomycin and metronidazole. A randomized, placebo-controlled trial, Ann. Intern. Med. 117(4):297–302; M. J. Zimmerman et al., Review article: treatment of Clostridium difficile infection, Aliment. Pharmacol. Ther. 11(6):1003–12 [1997]).

Teicoplanin is another antibiotic found to be effective against gram positive anaerobes such as Propionibacterium acnes, Clostridium perfringens, C. difficile, and other Clostridium spp., Peptococcus spp., Peptostreptococcus spp. (H. Hassan et al., In vitro activity of teicoplanin, vancomycin, A16686, clindamycin, erythromycin and fusidic acid against anaerobic bacteria, Singapore Med. J. 31(1):56–58 [1990]; The Swedish CDAD Study Group, Treatment of Clostridium difficile associated diarrhea and colitis with an oral preparation of teicoplanin; a dose finding study, Scand. J. Infect. Dis. 26(3):309–16 [1994]; C. Wenisch et al., Comparison of vancomycin, teicoplanin, metronidazole, and fusidic acid for the treatment of Clostridium difficile-associated diarrhea, Clin. Infect. Dis. 22(5):813–18 [1996]).

However, teicoplanin is not widely available. The peptide antibiotic bacitracin is also reported to be effective in treating C. difficile-induced diarrhea, but it is not widely available in an enteric formulation. (M. N. Dudley et al., Oral bacitracin vs. vancomycin therapyfor Clostridium difficile-induced diarrhea, A randomized double-blind trial, Arch. Intern. Med. 146(6):1101–04 [1986]).

Other adjunct treatments are reportedly effective for refractory C. difficile-related disease, including whole-bowel irrigation and enteric administration of the non-pathogenic yeast Saccharomyces boulardii. (C. A. Liacouras and D. F. A. Piccoli, Whole-bowel irrigation as an adjunct to the treatment of chronic, relapsing Clostridium difficile colitis, J. Clin. Gastroenterol. 22(3):186–89 [1996]; C. M. Surawicz, Clostridium difficile disease: diagnosis and treatment, Gastroenterologist 6(1):60–65 [1998]). But such treatments are uncomfortable or distasteful for many patients and are less suitable than easily administered antibiotics as a first line treatment regimen.

Accordingly, there remains a definite need for a modestly priced antimicrobial agent for treating gastrointestinal infections, without the commonly unpleasant side effects and bacteria resistance associated with metronidazole and vancomycin.

Pharmaceutical preparations of 4-(p)-aminosalicylic acid (i.e., 4-ASA or para-aminosalicylic acid) or 4-(p)-aminosalicylate sodium salt (e.g., Nemasol-Sodium® or Tubasal®) have been used systemically in cases of tuberculosis as antimicrobial chemotherapeutic agents against Mycobacterium tuberculosis.

On the other hand, the 5-aminosalicylates are known as anti-inflammatory chemotherapeutic agents and have not been used as antimicrobial agents. These compounds include 5-aminosalicylic acid (i.e., 5-ASA, mesalamine, or mesalazine) and conjugated derivatives thereof, known for their anti-inflammatory properties. These anti-inflammatory agents are commercially available in various pharmaceutical preparations such as Asacol®, Rowasa®, Claversal®, Pentasa®, Salofalk®, Dipentum®, Azulfidine® (SAZ) and others.

5-Aminosalicylates have been used widely to reduce mucosal inflammation in inflammatory bowel disease, ulcerative colitis and Crohn's disease. (S. B. Hanauer and FB. Baert, Medical Therapy of Inflammatory Bowel Disease, Inflamm. Bowel Dis. 78(6):1413–25 [1994]; C. J. Mulder et al., Drug therapy. dose-response relationship of oral mesalazine in inflammatory bowel disease, Mediators Inflamm. 7(3):135–36 [1998]; W. Kruis et al., Olsalazine versus mesalazine in the treatment of mild to moderate ulcerative colitis, Aliment. Pharmacol.12(8):707–15 [1998]; J. N. Healey, Gastrointestinal transit and release of mesalazine tablets in patients with inflammatory bowel disease, Scand. J. Gastroenterol. 172:47–51 [1990]).

The mechanism underlying the anti-inflammatory properties of the 5-aminosalicylates is unknown, but it may result from their ability to inhibit oxidation at the surface of endothelial membranes, perhaps through radical scavenging, and to prevent lipid peroxidation. (D. C. Pearson et al., The anti-oxidant properties of5-aminosalicylic acid, Free Radic. Biol. Med. 21(3):367–73 [1996]). 5-Aminosalicylates may be able to act synergistically with endogenous antioxidants such as alpha-tocopherol to prevent the oxidative damage implicated in the pathogenesis of inflammatory bowel diseases. (E. Goncalves et al., Antioxidant activity of 5-aminosalicylic acid against peroxidation of phosphotidylcholine liposomes in the presence of alpha-tocopherol: a synergistic effect?, Free Radic. Res. 29(1):53–66 [1998]).

There are several reports that 5-aminosalicylic acid also inhibits fimbriae-mediated cellular adhesion by enteroaggregative Escherischia coil strains, associated with both acute and persistent diarrhea in infants and children. (G. Kang et al., Salicylate inhibits fimbriae mediated Hep-2 cell adherence ofand haemagglutination by enteroaggregative Escherischia coli, FEMS Microbiol. Lett. 166(2):257–65 [1998]; D. Law and H. Chart, Enteroaggregative Escherischia coil, J. Appl. Microbiol. 84(5):685–97 [1998]; Y. Germani et al., Prevalence of enteropathogenic, enteroaggregative Escherischia coli among isolates from children with diarrhea in New Caledonia, J. Infect. Dis. 174(5):124–26 [1996]; S. Knutton et al., Ability of enteroaggregative Escherischia coil strains to adhere in vitro to human intestinal mucosa, Infect. Immun. 60(5):2083–91 [1992]).

Antimicrobial growth inhibitory properties of the 5-aminosalicylates and other features and advantages of the present invention will be described herein.

SUMMARY OF THE INVENTION

The method of the present invention employs the antimicrobial properties of 5-aminosalicylates in a method of inhibiting bacterial growth in a human or non-human vertebrate. By administering to a patient a pharmaceutical composition comprising a 5-aminosalicylate, the growth of bacterial species can be arrested, including the growth of anaerobic pathogens of the genus Clostridium, for example, *C. perfringens, C. difficile, C. botulinum* and *C. tetani*. The present method can be used to treat the gastrointestinal tract or any other non-gastrointestinal body site or tissue to inhibit bacterial growth.

The present method also has veterinary applications and can be used to treat a wide variety of non-human vertebrates, including wild, domestic and farm animals.

The present invention is also related to an antimicrobial method for inhibiting the growth of a bacterial species in a foodstuff and to foodstuffs containing a 5-aminosalicylate compound, useful for preventing food poisoning or botulism. The present invention is also related to food containers and food-handling implements with bacteriostatic properties, intended for holding a foodstuff, and to cleansers, polishes, paints, sprays, soaps, and detergents for inhibiting the growth of a bacterial species on surfaces.

The 5-aminosalicylates are generally well-tolerated and competitively priced compounds that can fill a definite need for an antimicrobial agent, which is selectively effective against gastrointestinal and non-gastrointestinal clostridial diseases.

These and other advantages and features of the present invention will be described more fully in a detailed description of the preferred embodiments which follows.

DETAILED DESCRIPTION OF THE PREFERRED EMBODIMENTS

The present invention is directed to the use of 5-aminosalicylates as antimicrobial agents in a method of inhibiting bacterial growth in a human or non-human vertebrate, in the gastrointestinal tract or any other body site or tissue. The method involves administering to a human or non-human vertebrate subject a pharmaceutically acceptable composition of the present invention.

The pharmaceutically acceptable compositions in accordance with the present invention are formulated for acceptable delivery to a human or non-human vertebrate gastrointestinal tract or other body site or tissue. Topical delivery to gastrointestinal mucosa and/or systemic delivery thereto are intended. Also included are pharmaceutically acceptable formulations for systemic or topical delivery to a non-gastrointestinal body site or tissue subject to bacterial growth, and particularly subject to clostridial growth.

The present invention is also related to pharmaceutically acceptable compositions containing a 5-aminosalicylate compound.

Five-aminosalicylate compounds include 5-aminosalicylic acid or any compound containing a 5-aminosalicylate moiety, or any conjugated derivative thereof, that is effective in inhibiting the growth of a bacterial species in a human or non-human vertebrate gastrointestinal tract or any other body site, limb, organ, such as heart, lung or kidney, or any other tissue of a vertebrate body.

A most preferred 5-aminosalicylate compound is 5-aminosalicylic acid, also known as mesalamine or mesalazine, and commercially available, for example, in pharmaceutical preparations known as Asacol® (Procter and Gamble), Pentasa ®(Ferring A/S Vanlose), Claversal®, Mesasal®, Rowasa®, and Salofalk® (Dr. Falk GmbH). (R. N. Brogden and E. M. Sorkin, Mesalazine. A review of its pharmacodynamic and pharmacokinetic properties, and therapeutic potential in chronic inflammatory bowel disease, Drugs 38(4):500–23 [1989]).

Also preferred are 5-aminosalicylate salts, including the sodium or potassium salts of conjugated 5-aminosalicylates.

Other preferred 5-aminosalicylate compounds, for purposes of the present invention, are compounds containing a 5-aminosalicylic acid moiety, or a 5-aminosalicylate moiety, conjugated to another 5-aminosalicylic acid moiety or 5-aminosalicylate moiety, or conjugated to a pharmaceutically acceptable carrier molecule.

Preferred conjugated 5-aminosalicylate compounds include, but are not limited to, olsalazine or Poly-ASA. Olsalazine is known variously as disodium-diazosalicylate, azodisalicylate, or Dipentum® (Pharmacia). Olsalazine comprises two 5-aminosalicylate moieties linked through a diazobond. Poly-ASA comprises a water-soluble polymer that contains 5-aminosalicylate moieties linked through diazobonds to an inert sulfanilamide ethylene polymer. (F. Martin, Oral 5-aminosalicylic acid preparations in treatment of inflammatory bowel disease: an update, Digestive Dis. Sci. 32(12 Suppl.):57S–63S [1987]; H. Allgayer, Sulfasalazineand 5-ASA compounds, GastrointestinalPharmacol. 21(3):643–658 [1992]).

Balsalazide (balsalazine) is another preferred conjugated 5-aminosalicylate compound. (J. R. Green et al., Balsalazide is more effective and better tolerated than mesalamine in the treatment of acute ulcerative colitis. The Abacus Investigator Group, Gastroenterol. 114(1):15–22 [1998*a*]; J. R. Green et al., Maintenance and remission of ulcerative colitis: a comparison between balsalazide 3 g and mesalamine 1.2 g daily over 12 months. Abacus Investigator Group, Aliment. Pharmacol. Ther. 12(12):1207–16 [1998]*b*).

Another preferred conjugated 5-aminosalicylate compound is sulphasalazine, also known as sulfasalazine, salazosulfapyridine, or Azulfidine®, in which a 5-aminosalicylic acid moiety is linked through a diazobond to sulfapyridine, the carrier molecule. (H. P. Osterwald, Pharmaceutic development: mesalazine, Scand. J. Gastroenterol Suppl. 172:43–46 [1990]). The skilled practitioner will be aware that patients to whom sulphasalazine is administered should be monitored especially carefully for symptoms of drug intolerance or hypersensitivity reactions that can occur in some patients. These symptoms are related to the sulfapyridine moiety and may include headache, nausea, vomiting, fever, rash, epidermolysis, hemolytic anemia, pancreatitis, pulmonary fibrosis, agranulocytosis, or liver toxicity; the use of sulphasalazine should be discontinued immediately when these symptoms occur. (S. B. Hanauer and G. Stathopoulos, Risk-benefit assessment of drugs used in the treatment of inflammatory bowel disease, Drug Saf. 6(3):192–219 [1992]; H. Allgayer [1992]). Impairment of male fertility is another possible side effect of sulphasalazine related to sulfapyridine. V. A. Botoman and G. F. Bonner, Management of inflammatory bowel disease, Am. Fam. Physician 57(l):57–68 [1998]).

Other preferred conjugated 5-aminosalicylate compounds are ipsalazine (ipsalazide) and salicylazobenzoic acid; these are also well tolerated molecules comprising a 5-aminosalicylic acid moiety or 5-aminosalicylate moiety linked by a diazobond to another pharmaceutically acceptable chemical unit. (M. C. Rijk et al., Disposition of mesalazine-delivering drugs in patients with inflammatory bowel disease, with and without diarrhoea, Scand. J. Gastroenterol. 27(10):863–68 [1992]; S. N. Rasmussen, Bioavailability of controlled release mesalazine [5-ASA] preparations, J. Gastroenterol. 30(Suppl. 8):112–114 [1995]).

Other preferred conjugated 5-aminosalicylate compounds for gastrointestinal use are bile acids conjugated with a 5-aminosalicylic acid moiety or 5-aminosalicylate moiety. For example, in ursodeoxycholic acid-5-aminosalicylic acid (UDCA-5-ASA), ursodeoxycholic acid is linked through an amide bond to 5-aminosalicylic acid. The conjugated 5-aminosalicylate compound is synthesized by adding a basic solution of 5-aminosalicylic acid into the mixed anhydride of ursodeoxycholic acid and ethyl chloroformate. (A. K. Batta et al., Synthesis and intestinal metabolism of ursodeoxycholic acid conjugate with an antiinflammatory agent, 5-aminosalicylic acid, J. Lipid Res. 39(8);1641–46 [1998]). Five-aminosalicylate bile acid conjugates are not substantially absorbed in the duodenum but can be partially hydrolyzed in the colon by intestinal bacteria, such as *Clostridium perfringens*, to ursodeoxycholic acid and 5-aminosalicylic acid. Id.

As the skilled artisan is aware, bacterial azoreductases can reduce diazo bonds linking 5-aminosalicylic acid or 5-aminosalicylate moieties to another chemical moiety, thus releasing 5-aminosalicylic acid or 5-aminosalicylate. Similarly, certain hydrolases, e.g., cholylglycine hydrolase, can deconjugate 5-aminosalicylic acid moieties or 5-aminosalicylate moieties from other carriers, such as bile acids. Other particular varieties of 5-aminosalicylate conjugate can be subject to deconjugation by other enzyme systems. Whether or not a 5-aminosalicylic acid or 5-aminosalicylate moiety is actually deconjugated from a carrier molecule or from another 5-aminosalicylate moiety, in a human or non-human vertebrate gastrointestinal tract or other body site, does not limit the embodiments of a 5-aminosalicylate compound contemplated by the present invention. The present invention is not committed to any particular mechanism by which a particular 5-aminosalicylate compound operates to inhibit bacterial growth.

The 5-aminosalicylate compound is administered by any suitable method. Representative methods include giving, providing, feeding or force-feeding, dispensing, inserting, prescribing, furnishing, treating with, taking, swallowing, eating or applying a pharmaceutical composition of the present invention.

As well as a 5-aminosalicylate compound, the pharmaceutical compositions of the present invention can optionally contain pharmaceutically acceptable solvent(s), adjuvant(s) or non-medicinal carrier(s), binder(s), thickener(s), or filler substance(s) that are known to the skilled artisan. Common fillers include, but are not limited to, sucrose or lactose, or polymeric substances like starch. Also contemplated are additional medicinal or nutritive additives in combination with a 5-aminosalicylate compound, as may be desired to suit the more particular needs of the practitioner.

A dose effective to inhibit the growth of a bacterial species is such dose as sufficient to prevent cellular proliferation of a bacterial species, by either killing bacterial cells or by preventing or slowing cellular growth or reproduction of a bacterial species, compared to the rate of growth or reproduction in the absence of a 5-aminosalicylate compound. By way of example, 12.5 mg or more of 5-aminosalicylic acid have been found sufficient to inhibit the growth of *Clostridium perfringens* on 10-mL blood agar plates.

The effective dose for each human or non-human vertebrate subject will depend upon the size and physiologic reactions of the subject to whom or to which the pharmaceutical preparations of the present invention are administered. And these reactions and the antimicrobial activity of the administered dose can be monitored by the prescribing physician or veterinarian. The pharmaceutical compositions of the present invention can be formulated and manufactured at more than one concentration, such that modular incremental amounts of 5-aminosalicylate compound are easily administered.

For example, currently available preparations of 5-aminosalicylate compounds can be obtained in variable dosage units, including, for example: 250 mg (e.g., Salofalk®, Pentasa®, Azulfadine®, Dipentum®, or olsalazine); 400 mg (e.g., Asacol®); 0.5, 1.5 g or 3.0 g (e.g., Pentasa®, Rowasa®, Azulfadine®, balsalazide). Suppositories containing 5-aminosalicylic acid in dosage units ranging from 0.2 to 1.0 grams are also available; enema solutions containing 1 to 4 g of 5-aminosalicylic acid are also known. (M. A. Peppercorn, Advances in drug therapy for inflammatory bowel disease, Ann. Intern. Med. 112:50–60 [1990]).

The foregoing are merely illustrative of the possible dosage units that can be employed in the pharmaceutical compositions of the present invention, and smaller or larger dosage units than these are also contemplated. Larger dosage units are especially useful for large non-human vertebrates, such as, but not limited to, bovine animals, horses, pachyderms, or large marine mammals; smaller dosage units are especially useful for pediatric application and for small vertebrates, such as, but not limited to, mice or chickens.

A minimum effective dose is as little as between 6.25 and 12.5 mg of a 5-aminosalicylate compound per day. Effective doses of a 5-aminosalicylate compound at 12.5 to 150 mg per day and 150 to 250 mg per day are sufficient for smaller human adults, children, and smaller non-human vertebrates, such as rodents, canines, chickens and turkeys. A higher effective dose for an adult human is 250–6400 mg of a 5-aminosalicylate per day. Pediatric doses are typically 10–20% of effective doses for adult humans. Higher effective doses, from 6,450 mg/day, up to 1,000 mg/kg body mass per day can be used for large non-human vertebrates, for example, for sheep and larger animals such as cattle, horses, and elephants.

Antimicrobial activity by 5-aminosalicylate compounds against a specific bacterial species of interest is determined by routine means well known to the skilled practitioner. For example, a "lawn" of a bacterial species can be plated on an appropriate solid medium, and zones of growth inhibition around sterile cellulose disks impregnated with a 5-aminosalicylate compound of interest can be measured. Similarly, inhibition assays in liquid media are also routinely accomplished.

Inhibition of bacterial growth in a gastrointestinal tract is measured by conventional means well known to the skilled artisan. Many fermentative bacterial species found in the gastrointestinal tract produce detectable quantities of hydrogen or methane gas in the presence of certain sugars, which gases enter the blood stream of the host and are exhaled. This is the basis for intestinal bacterial growth detection means, such as, but not limited to, the lactulose, glucose, or lactose breath hydrogen tests. (E.g., P. Kerlin and L. Wong, Breath hydrogen testing in bacterial overgrowth of the small intestine, Gastroenterol. 95(4):982–88 [1988]; A. Strocchi et al., Detection of malabsorption of low doses of carbohydrate: accuracy of various breath $H_2$ criteria, Gastroenterol. 105(5):1404–1410 [1993]).

Alternatively, bacterial growth in a gastrointestinal tract is measured by detection of $^{13}CO_2$ or $^{14}CO_2$ breath emissions after administering an isotope-labeled sugar that is metabolizable by gastrointestinal bacteria but non-digestible by the host, such as, but not limited to, xylose or lactulose in humans. (E.g., G. R. Swart and J. W. van den Berg, $^{13}C$ breath test in gastrointestinal practice, Scand. J. Gastroenterol. [Suppl.] 225:13–18 [1998]; C. E. King and P. P. Toskes, Breath tests in the diagnosis of small intestinal bacterial overgrowth, Crit. Rev. Lab. Sci. 21(3):269–81 [1984]; C. S. Chang et al., Increased accuracy of the carbon-14 D-xylose breath test in detecting small-intestinal bacterial overgrowth by correction with the gastric emptying rate, Eur. J. Nucl. Med. 22(10):1118–22 [1995]; A. Schneider et al., Value of the $^{14}C$–D-xylose breath test in patients with intestinal bacterial overgrowth, Digestion 32(2):86–91 [1985]).

Direct gastrointestinal sampling or biopsy from any body site or tissue can also be used to measure the inhibition of bacterial growth in a gastrointestinal tract or other body site or tissue. As the skilled artisan is aware, direct sampling at time intervals provides information about the growth inhibition of specific bacterial species of interest, to which breath testing is not well-suited. Samples are diluted and bacterial numbers can be assessed by conventional microbiological means such as, but not limited to colony plating or Most Probable Number (MPN) techniques, or direct counting of bacterial cells. For direct bacterial cell counts, cells can optionally be labeled with specific markers, and counts can be accomplished manually or by devices such as fluorescence activated cell sorting (FACS).

Alternatively, evidence of inhibition of bacterial growth can be inferred by the practitioner treating a bacterial infection or intestinal bacterial overgrowth in a human or nonhuman vertebrate subject with observation of an improvement in various infection-or overgrowth-related symptoms in response to the administration of an antimicrobial composition of the present invention.

Among the bacterial species inhibited in accordance with the present inventive method are obligate anaerobes such as, but not limited to, Clostridium species. It is a particular advantage of the present invention that 5-aminosalicylic acid is an antimicrobial agent that does not affect many beneficial or commensal gastrointestinal bacteria but selectively inhibits potentially pathogenic clostridial species, such as, but not limited to, C. perfringens, C. difficile, C. tetani and C. botulinum.

The method of the present invention is also useful for veterinary purposes. An antimicrobial composition comprising a 5-aminosalicylate compound can be administered to a non-human vertebrate including, but not limited to, a wild, domestic or farm animal. The present method is useful for treating a mammal such as a non-human primate, mouse, rat, rabbit, gerbil, hamster, canine, feline, ovine, bovine, swine, pachyderm, equine, or marine mammal. Also, the method is useful to inhibit the growth of bacteria in a bird (avian) or poultry, such as a duck, chicken, goose, turkey, ostrich, emu, dove, pigeon, quail, pheasant, peafowl, or guinea fowl.

In one embodiment, the pharmaceutically acceptable composition is administered by a non-systemic delivery route to the site of bacterial infection or overgrowth that is not primarily by way of the blood stream of a human or non-human vertebrate.

Some non-systemic delivery routes and pharmaceutically acceptable non-systemic delivery systems that could be employed by one of skill in the art in practicing the methods and compositions of the present invention are now exemplified. The following are presented merely to illustrate and in no way to limit the possible delivery means contemplated.

For gastrointestinal bacterial infection or bacterial overgrowth, suitable non-systemic delivery routes include, but are not limited to, an ingestive delivery route or a colonic delivery route. A most preferred delivery route is an ingestive delivery route, whereby the antimicrobial agent enters the gastrointestinal or digestive tract by way of voluntary or forced ingestion through the mouth. The organs of a gastrointestinal tract include the esophagus, stomach, large intestine, small intestine, or rectum. The skilled artisan will be aware that in a non-human vertebrate the digestive tract may include a rumen, crop, gullet, cecum, or other specialized organ as pertains to a particular vertebrate species.

Another non-systemic delivery route is useful for non-gastrointestinal bacterial infections, particularly infections of the skin or externally accessible wounds; this delivery route is topical application to the affected area of an antimicrobial cream, gel, or ointment.

Another preferred embodiment of the pharmaceutical compositions of the present invention, employing a non-systemic delivery route, is a suppository or foam for delivery of a composition comprising a 5-aminosalicylate compound via anus or rectum to the colon. Once delivered, a 5-aminosalicylate compound of the present invention will act topically at the intestinal mucosa. Such suppository or foam delivery systems are known in the art; a commercially available example is Rowasa® mesalamine suppositories for anti-inflammatory purposes. Together with a 5-aminosalicylate compound the pharmaceutical preparation of the present invention, such as a suppository, can employ a variety of conventional thickeners, such as alginate, xanthan gum, or petrolatum. Also contemplated are suppositories or foams comprising hydrophilic polymers, such as hydroxypropyl cellulose, hydroxypropyl methylcellulose, hydroxyethylcellulose, dextran, pectin, polyvinyl pyrrolidone, starch, gelatin, or any of a number of other polymers known to be useful for this purpose.

Another preferred embodiment of the compositions of the present invention is a gel for non-systemic delivery of a composition comprising a 5-aminosalicylate compound via the colon, similar to gels commonly used for the delivery of other chemotherapeutic agents. Hydrogel matrices are known for this purpose. (Feijen, Biodegradable hydrogel matrices for the controlled release of pharmacologically active agents, U.S. Pat. No. 4,925,677). Such biodegradable gel matrices may be formed, for example, by cross-linking a proteinaceous component and a polysaccharide or mucopolysaccharide component, then loading with a 5-aminosalicylate compound, for deliverability over an extended period.

Another preferred embodiment of the present pharmaceutical composition formulated for a colonic non-systemic delivery system is a composition comprising a 5-aminosalicylate compound in an osmotically suitable enema solution. Commercially available preparations include Rowasa® mesalamine enemas for anti-inflammatory purposes. (See, R. N. Brogden and E. M. Sorkin, Mesalazine. A review of its pharmacodynamic and pharmacokinetic properties, and therapeutic potential in chronic inflammatory bowel disease, Drugs 38(4):500–24 [1989]).

A most preferred embodiment of the pharmaceutical composition of the present invention is formulated for a non-systemic ingestive delivery system, such as, but not limited to a tablet, capsule, or caplet.

Preferably, the non-systemic ingestive delivery system comprises an enteric coating to prevent esophageal or gastric release of 5-aminosalicylate compound. Such enteric-coated pharmaceuticals disintegrate after leaving the stomach, resulting in drug dispersion in the small intestine or colon where 5-aminosalicylates will act topically at the intestinal mucosa. As the skilled artisan will be aware, enteric-coated drug delivery systems are typically pH-sensitive, polymer-coated tablets, capsules, or caplets. A polymer coating can be selected that will direct release of a 5-aminosalicylate compound to a particular region of the gut. Such polymers include, but are not limited acrylic polymers such as Eudragit-L or Eudragit-S, and cellulosic polymers, such as ethylcellulose.

Commercially available examples of enteric-coated 5-aminosalicylates are mesalamine preparations known as Asacol® and Claversal®, used as anti-inflammatory agents. The acrylic polymer coating of Claversal®, starts to dissolve at pH 6.0 after passing through the far more acidic milieu of the stomach, and as a result, mesalamine is reliably released in the distal small intestine (ileum) and colon of a human patient. (H. P. Osterwald, Pharmaceutic development: mesalazine, Scand. J. Gastroenterol. Suppl. 172:43–46 [1990]; D. Claussen, Asacol [mesalamine], Gastroenterol. Nurs. 15(l):33–34 [1992]). The acrylic polymer coating (i.e., Eudragit-S) of Asacol® is degraded at above pH 7.0. Thus, it is carried to the right side of the human colon where intraluminal pH is elevated above 7.0. (M. J. Dew et al., An oral preparation to release drug in the human colon, Br. J. Clin. Pharmacol. 14:405–08 [1982]). Salofalk® is another example; it is coated first with a semipermeable layer of ethylcellulose and second with an acrylic polymer (i.e., Eudragit-L), which is degraded at above pH 5.6 in the distal small intestine and colon to release mesalamine there. (F. Martin [1987]).

Pentasa® contains 5-aminosalicylic acid microgranules coated with a semipermeable membrane of amphionic ethylcellulose, which can dissolve at either acidic or basic pH to release the microgranules. (F. Martin [1987]).

In addition, such tablets, capsules, or caplets can be formulated in a multi-layer configuration for slow release over an extended period. Again, Pentasa® is an example of a commercially available ingestible slow release form of a 5-aminosalicylate compound. (See P. Fockens et al., Comparison ofthe efficacy and safety of 1.5 compared with 3.0 g oral slow release mesalazine [Pentasa] in the maintenance treatment of ulcerative colitis. Dutch Pentasa Study Group, Eur. J. Gastroenterol. Hepatol. 7(11):1025–30 [1995]).

Another preferred ingestive delivery system comprises a lavage system, whereby a patient will ingest a large volume of an osmotically balanced flushing solution, containing 5-aminosalicylic acid, or a conventional flushing solution in conjunction with another ingestible form of a 5-aminosalicylate antimicrobial agent. Such a lavage system can virtually eliminate bacterial populations from the intestine. This may be especially desirable in refractory cases of bacterial overgrowth or in preparing a patient for abdominal surgery.

Another preferred ingestive delivery system is especially, but not exclusively, useful for veterinary applications. In this embodiment a pharmaceutical preparation of the present invention is formulated and prepared to be ingested by an animal along with its food, as part of a pharmaceutically acceptable feed mixture. A pharmaceutically acceptable food additive for humans is also contemplated.

For some applications, a preferred embodiment of the antimicrobial method of the present invention involves a systemic delivery route, i.e., a route whereby delivery of a 5-aminosalicylate compound to the site of infection or bacterial growth is primarily via the blood stream. This embodiment can be used to inhibit bacterial growth in any body site or tissue, including the gastrointestinal tract. A systemic delivery route is also particularly, but not exclusively useful for gastrointestinally infected patients who are unable to effectively ingest a non-systemic formulation of the composition of the present invention due to persistent nausea, difficulty in swallowing, or other ingestion-preventing conditions, or who, due to resection or other condition of the bowel cannot accept a colonic delivery system.

Alternatively, a systemic delivery route can be employed to deliver a 5-aminosalicylate compound to body sites or tissues other than those of the gastrointestinal tract, including, but not limited to, skin, heart, lung, blood, kidney, liver, brain, arms, legs, digits, sexual organs, trunk, head, neck, or tail. Applications can include but are not limited to treating or preventing clostridial infections at any body site or tissue of a vertebrate. Such clostridial infections include, but are not limited to, gangrene or tetanus, caused, respectively, by C. perfringens and C. tetani, when these species grow in wounds and damaged tissues with low oxygen tension.

Entry of a 5-aminosalicylate compound into the blood stream of a human or non-human vertebrate patient can occur by any route, system, device, method or mechanism. For the purposes of the present invention, a systemic delivery route can also include delivery through the skin, mucosa or epithelium of the mouth including the sublingual epithelium, the rectum, or the vaginal epithelium.

Systemic delivery systems that are contemplated by the present invention include, but are not limited to, ingestion, injection, or intravenous drip, most conventionally. Other useful systemic delivery systems are known and include, but are not limited to, implant; adhesive transdermal patches; topical creams, gels or ointments for transdermal delivery; transmucosal delivery matrices or suppositories or gels. It is contemplated that the compositions of the present invention are formulated to deliver an effective dose of a 5-aminosalicylate compound by these or any other pharmaceutically acceptable systemic delivery system.

A preferred embodiment of the compositions of the present invention employing a systemic delivery route is a topical cream, ointment or gel to be applied to the skin. In this embodiment, a composition of the present invention comprises a 5-aminosalicylate compound in a pharmaceutically acceptable delivery system comprising a permeation or penetration enhancer, such as polyethylene glycol monolaurate, dimethyl sulfoxide, N-vinyl-2-pyrrolidone, N-(2-hydroxyethyl)-pyrrolidone, or 3-hydroxy-N-methyl-2-pyrrolidone. A variety of conventional thickeners often used in creams, ointments and gels, such as, but not limited to, alginate, xanthan gum, or petrolatum, may also be employed in this embodiment of a composition of the present invention.

Another preferred embodiment of the compositions of the present invention is a formulation for systemic transmucosal delivery of a 5-aminosalicylate compound. A variety of pharmaceutically acceptable systems for transmucosal delivery of therapeutic agents are known in the art and are compatible with the practice of the present invention. (Heiber et al., Transmucosal delivery of macromolecular drugs, U.S. Pat. Nos. 5,346,701 and 5,516,523; Longenecker et al., Transmembrane formulations for drug administration, U.S. Pat. No. 4,994,439). Transmucosal delivery devices may be in free form, such as a cream, gel, or ointment, or may comprise a determinate form such as a tablet, patch, or troche. For example, delivery of a 5-aminosalicylate compound may be via a transmucosal delivery system comprising a laminated composite of, for example, an adhesive layer, a backing layer, a permeable membrane defining a reservoir containing a 5-aminosalicylate compound a peel seal disc underlying the membrane, one or more heat seals, and a removable release liner. (Ebert et al., Transdermal delivery system with adhesive overlay and peel seal disc, U.S. Pat. No. 5,662,925; Chang et al., Device for administering an active agent to the skin or mucosa, U.S. Pat. Nos. 4,849,224 and 4,983,395).

Alternatively, a tablet or patch for delivery through the oral mucosa can comprise an inner layer containing the therapeutic agent of choice, a permeation enhancer, such as a bile salt or fusidate, and a hydrophilic polymer, such as hydroxypropyl cellulose, hydroxypropyl methylcellulose, hydroxyethylcellulose, dextran, pectin, polyvinyl pyrrolidone, starch, gelatin, or any of a number of other polymers known to be useful for this purpose. This inner layer can have one surface adapted to contact and adhere to the moist mucosal tissue of the oral cavity and may have an opposing surface adhering to an overlying non-adhesive inert layer. Optionally, such a transmucosal delivery system can be in the form of a bilayer tablet, in which the inner layer also contains additional binding agents, flavoring agents, or fillers. Some useful systems employ a non-ionic detergent along with a permeation enhancer. These examples are merely illustrative of available transmucosal delivery technology and are not limiting of the present invention.

Another preferred embodiment of the compositions of the present invention is a gel for systemic delivery of a 5-aminosalicylate via the rectal or vaginal mucosa, similar to gels commonly used for the delivery of various other therapeutic agents. Hydrogel matrices are known for this purpose. (Feijen, Biodegradable hydrogel matricesfor the controlled release of pharmnacologically active agents, U.S. Pat. No. 4,925,677). Such biodegradable gel matrices can be formed, for example, by cross-linking a proteinaceous component and a polysaccharide or mucopolysaccharide component, then loading with a 5-aminosalicylate compound to be delivered.

Another preferred embodiment of the compositions of the present invention is the systemic delivery of a 5-aminosalicylate compound via a biodegradable matrix implanted within the body or under the skin of a human or non-human vertebrate. The implant matrix may be a hydrogel similar to those described above. Alternatively, it may be formed from a poly-alpha-amino acid component. (Sidman, Biodegradable, implantable drug delivery device, and process for preparing and using same, U.S. Pat. No. 4,351,337).

A preferred embodiment of the composition of the present invention employing a systemic delivery route is a transdermal delivery system of a kind known in the art for delivering various drugs. Transdermal delivery systems can be of any number of varieties known in the art. For example, delivery of a 5-aminosalicylate compound can be via a transdermal delivery system comprising a laminated composite of an adhesive layer, a backing layer, a permeable membrane defining a reservoir containing a 5-aminosalicylate compound, a peel seal disc underlying the membrane, one or more heat seals, and a removable release liner. (Ebert et al., Transdermal delivery system with adhesive overlay and peel seal disc, U.S. Pat. No. 5,662,925; Chang et al., Device for administering an active agent to the skin or mucosa, U.S. Pat. Nos. 4,849,224 and 4,983,395).

Alternatively, a transdermal delivery device can be a matrix type transdermal patch. (Chien et al., Transdermal estrogen/progestin dosage unit, system and process, U.S. Pat. Nos. 4,906,169 and 5,023,084; Cleary et al., Diffusion matrix for transdermal drug administration and transdermal drug delivery devices including same, U.S. Pat. No. 4,911,916; Teillaud et al., EVA-based transdermal matrix system for the administration of an estrogen and/or a progestogen, U.S. Pat. No. 5.605,702; Venkateshwaran et al., Transdermal drug delivery matrix for coadministering estradiol and another steroid, U.S. Pat. No. 5,783,208; Ebert et al., Methods for providing testosterone and optionally estrogen replacement therapy to women, U.S. Pat. No. 5,460,820). The matrix of the patch can comprise a basal support layer, such as an acrylic or ethylene/vinyl acetate copolymer or a polyurethane foam or cellulosic material, and an adhesive, such as, but not limited to, polysiloxane. In the compositions of the present invention, the polymer matrix also contains a 5-aminoslaicylate compound, as described above, and optionally, a penetration-enhancing vehicle or carrier, such as N-vinyl-2-pyrrolidone, N-(2-hydroxyethyl)-pyrrolidone, or 3-hydroxy-N-methyl-2-pyrrolidone. The adhesive patch may be pressure-sensitive, to release the 5-aminosalicylate compound across the skin of the patient when the patch matrix has been applied to the skin. The patch may optionally comprise an inert backing layer in addition to a matrix layer, or can comprise multiple dosage units or layers.

The present invention is also related to a method of inhibiting the growth of a bacterial species on a foodstuff. A foodstuff for purposes of the present invention is any food or beverage that can be ingested. This method is intended for bacteriostatic food packaging or handling and relies on the antimicrobial properties of 5-aminosalicylates. The present method involves treating a food-contacting surface of a material that is pharmaceutically acceptable for food packaging or food handling purposes, with a 5-aminosalicylate compound in an amount effective to inhibit the growth of a bacterial species on a food contacting the surface.

Acceptable materials for food packaging or handling include, but are not limited to, paper, wood, cardboard, or other cellulosic polymers, including transparent and non-transparent cellulosic polymers; plastic polymers; waxes; glass or silica; pottery, earthenware, or other ceramic; or metallic materials.

A food-contacting surface of a suitable polymeric material is treated with a 5-aminosalicylate compound by enmeshing, implanting, or impregnating the compound within the polymeric material, by means known to the artisan skilled in food packaging and handling materials.

Alternatively, a suitable polymeric material is treated with a 5-aminosalicylate compound by covalent linkage, such as by conjugation of the 5-aminosalicylate compound to the polymeric material through, for example, diazo bonds or amide bonds.

Alternatively, a polymeric or non-polymeric material is treated with a 5-aminosalicylate compound by coating the material with a coating formulation suitable for a desired coating means, such as, but not limited to, dipping, spraying or brushing onto a surface intended for food contact. A suitable coating formulation contains, in addition to a 5-aminosalicylate compound, an appropriate carrier(s), which carriers are known in the art. For example, the skilled practitioner can employ as a carrier a non-toxic polymeric resin, additionally containing an effective amount of a 5-aminosalicylate compound, which resin can be used to coat the food-contacting surface of the material, hardening in place upon it.

An effective amount of a 5-aminosalicylate compound for treating the food-contacting surface of the material is between 0.1 and 10 mg per cm$^2$ of the surface. Most preferably, the amount of 5-aminosalicylate compound is 0.4 to 2 mg per cm$^2$ of the surface. This is sufficient concentration to inhibit the growth of a food-poisoning or botulism-causing bacterial species as demonstrated in the detailed examples described herein. While the amount of the 5-aminosalicylate compound on the food-contacting surface of the material is relatively low, it is preferable not to use sulphasalazine as the 5-aminosalicylate compound, due to the possibility of sulfapyridine-related reactions in a minority of food consumers, as described above. Also, it is preferable not to use a 5-aminosalicylate-conjugated bile acid, as this may adversely affect the stability or taste of the food contacting the surface.

The present invention is also related to food containers and food-handling implements for holding a foodstuff, which includes containing, packaging, covering, storing, displaying, processing, cutting, chopping, impaling, kneading, manipulating or otherwise handling the foodstuff, such that a surface of the food container or implement comes in contact with the foodstuff, The present food containers and food-handling implements comprise a material suitable for contact with food and have a food-contacting surface treated with a 5-aminosalicylate compound, as described above, in an amount effective to inhibit the growth of a bacterial species. The containers and implements are in any suitable disposable (i.e., single-use) or non-disposable (i.e., multi-use) configuration capable of holding a foodstuff. These configurations include, but are not limited to, foils, shear wraps, sheets, papers, waxed papers, bags, cartons, trays, plates, bowls, covered and uncovered storage vessels, serving dishes, cups, cans, jars, bottles, or any other suitable container configuration for a particular foodstuff. Additional configurations especially useful for food handling purposes include, but are not limited to, gloves or mitts; utensils such as forks, spoons, knives, slicers, processors, juicers, grinders, chippers, hooks, presses, screws, openers, cutters, peelers, tongs, ladles, scoops, cups, chutes or spatulas; and cutting boards, kneading boards, mixing bowls, drying or cooling racks, or shelves.

The present method, containers, and implements are especially useful in inhibiting the growth of bacterial species that can release pathogenic exotoxins, such as, but not limited to, *Clostridium perfringens*, or *Clostridium botulinum*, the exotoxins of which cause botulism. They are especially, but not exclusively, useful in commercial and institutional food preparation contexts where food is handled and packaged in bulk, such as, but not limited to, food processing factories, canning plants, slaughterhouses, restaurants, cafeterias, salad bars, grocery outlets, and hospitals. The present method, containers and implements are useful for any kinds of foodstuff. They are particularly useful in situations where food is processed, packaged, stored, or displayed at a temperature, at or above room temperature, but insufficiently hot to kill bacterial cells and spores, for example, when food is kept under a warming light. But the present method, containers and implements are also useful in the home kitchen.

The present invention is also related to antimicrobial cleansers, polishes, paints, sprays, soaps, or detergents formulated for application to surfaces to inhibit the growth of a bacterial species thereon. These surfaces include, but are not limited to surfaces, such as, countertops, desks, chairs, laboratory benches, tables, floors, bed stands, tools or equipment, doorknobs, and windows. The present cleansers, polishes, paints, sprays, soaps, or detergents contain a 5-aminosalicylate compound that provides a bacteriostatic property to them. They can optionally contain suitable solvent(s), carrier(s), thickeners, pigments, fragrances, deodorizers, emulsifiers, surfactants, wetting agents, waxes, or oils. A preferred embodiment is a formulation for external use as a pharmaceutically acceptable skin cleanser, particularly for the surfaces of human hands.

In the present cleansers, polishes, paints, sprays, soaps, and detergents, the concentration of the 5-aminosalicylate compound is between 0.625 and 200 mg per mL. Most preferably the concentration of 5-aminosalicylate compound is 1.25 to 50 mg per mL.

The present cleansers, polishes, paints, sprays, soaps, and detergents are useful in homes and institutions, particularly but not exclusively in hospital settings for the prevention of nosocomial infections.

The present invention is also related to an antimicrobial method for inhibiting the growth of a bacterial species in a foodstuff and to foodstuffs containing a 5-aminosalicylate compound. Bacterial growth in foodstuff, if uninhibited, can result in the release of bacterial exotoxins that can cause illness or death in a human or non-human vertebrate that consumes the foodstuff. The present method and foodstuffs are particularly useful in preventing clostridial food poisoning by, for example, *Clostridium perfringens*, or by Clostridium botulinum, the exotoxins of which cause botulism.

The present method employs a 5-aminosalicylate compound added to the foodstuff. Any foodstuff can be treated using the present method, but foods for which the present method is especially useful include non-acidic foods, such as mayonnaise or other egg products, potato products, and other vegetable or meat products. Five-aminosalicylates are autoclavable and thus may be used effectively in canned foods.

The 5-aminosalicylate compound for adding to the foodstuff can be part of any comestible formulation that can also include a suitable medium or carrier for convenient mixing or dissolving into a particular foodstuff. The medium or carrier is preferably one that will not interfere with the familiar flavor of the food of interest, such as are known by the artisan skilled in food processing techniques.

An effective amount of a 5-aminosalicylate compound to be added to a foodstuff is less than that required for administration to a vertebrate subject. The present foodstuffs contain a concentration of a 5-aminosalicylate compound between 0.625 and 10 mg per gram of the foodstuff. Most preferably the concentration of 5-aminosalicylate compound is 1.25 to 5 mg per gram of foodstuff. This is sufficient concentration to inhibit the growth of a food-poisoning or botulism-causing bacterial species as demonstrated in the detailed examples described herein.

While the concentration of the 5-aminosalicylate compound in the foodstuff is relatively low, it is again, preferable not to use sulphasalazine as the 5-aminosalicylate compound, due to the possibility of sulfapyridine-related reactions in a minority of food consumers, as described above. Also, it is preferable not to use a 5-aminosalicylate-conjugated bile acid, as this may adversely affect the stability or taste of the foodstuff before consumption.

The present antimicrobial method for inhibiting bacterial growth in a foodstuff and foodstuffs employing the antimicrobial properties of 5-aminosalicylates are useful alternative means of preventing food poisoning or botulism, instead of nitrite preservatives or gamma irradiation of food, which are disfavored by a sizeable number of consumers.

The methods and pharmaceutical compositions of the present invention provide a much needed addition to the antimicrobial armamentarium against bacterial overgrowths and infections, especially clostridial infections that affect great numbers of humans and animals worldwide. Five-aminosalicylate compounds are modestly priced relative to other antibiotics and are conveniently administered.

The administration of 5-aminosalicylates is well tolerated by the vast majority of patients with only rare side effects, which, of course, the practitioner should monitor in each individual patient. For example, 5-aminosalicylic acid is known to pose no substantial teratogenic risk in humans and can be administered safely to pregnant women. (O. Diav-Citrin et al., The safety of mesalamine in human pregnancy: a prospective controlled cohort study, Gastroenterol. 114(1):23–28 [1998]; P. Marteau et al., Foetal outcome in women with inflammatory bowel disease treated during pregnancy with oral mesalazine microgranules, Aliment. Pharmacol. Ther. 12(11):1101–08 [1998]; C. M. Bell and F. M. Habal, Safety of topical 5-aminosalicylic acid in pregnancy, Am. J. Gastroenterol. 92(12):2201–02 [1997]). The use of sulphasalazine requires closer monitoring, as mentioned above.

The foregoing applications for the methods and compositions of the present invention are illustrative and by no means exhaustive. The invention will now be described in greater detail by reference to the following non-limiting examples.

EXAMPLES

The antimicrobial properties of a 5-aminosalicylate compound, mesalamine, were tested using five organisms, commonly, but not exclusively, found in gastrointestinal tracts.

Example 1

Bacterial Cultures

*Bacteroides fragilis* (Gram negative anaerobe), *Clostridium perfringens* (Gram positive obligate anaerobe), *Escherichia coli* (Gram negative facultative anaerobe), a Lactobacillus isolate (Gram positive aerotolerant anaerobe), and *Enterococcus faecalis* (Gram negative facultative anaerobe) were examined, because each produces a detectable gaseous fermentation product under certain anaerobic growth conditions. All cultures were maintained on standard blood agar plates ([g/L distilled $H_2O$]: pancreatic digest of casein, 15.0; papale digest of soybean meal, 5.0; NaCl, 5.0; agar, 20.0; yeast extract, 5.0; hemin, 0.003; vitamin K1, 0.01; L-cystine, 0.4; defibrinated sheeps' blood, 5.0%) at 37° C. in an anaerobic $CO_2$ chamber (Bacteroides, Lactobacillus and Clostridium) or aerobically (Escherichia and Enterococcus). Inocula for plating experiments were taken aseptically by probe from distinct colonies on culture plates that were no more than 72 hours (anaerobic) or 24 hours (aerobic) old.

Example 2

Plating and Colony Counting

Mesalamine was obtained commercially in the form of Asacol (Procter and Gamble). The entenic coating on 400 mg Asacol tablets was removed with acetone. After the coating was dissolved, intact tablets were air dried and sterilized by autoclaving at 121° C., 15 psi, for 15 minutes. The sterile tablets were aseptically dissolved in sterile distilled water.

One milliliter-aliquots of serial dilutions containing 0, 3.125, 6.25, 12.5, 25, 50, and 100 mg/mL of mesalamine in sterile distilled water were placed onto anaerobic and aerobic blood 10-mL agar plates. To facilitate impregnation into the agar, the plates were allowed to dry for about 6 hours.

Aliquots of 0.5 McFarland units of cell suspensions of each bacterial species were separately diluted 1:106 in sterile saline (0.15 M NaCl), and 1 mL of each diluted cell suspension was plated on 4 replicate plates at each concentration of mesalamine. All plates were incubated at 37° C. Plates inoculated with *E. coli* or *Enterococcus faecalis* were incubated aerobically for 24 hours, and plates inoculated with *C. perfringens*, *B. fragilis*, or Lactobacillus were allowed to incubate anaerobically in GasPak chambers for 48 hours. Colony counts were assessed from each of the four plates of each concentration of mesalamine for each species. Paired t-test was used to compare groups of readings. Four replicate control plates at each concentration of mesalamine were incubated as described above after plating with 1 mL of sterile saline. (All controls were negative for bacterial colonies.)

Example 3

Results

Resulting colony counts for *E. coli* and a *C. perfringens* isolate are tabulated in Table 1. In the concentration range between 12.5 and 100 mg/mL, mesalamine inhibited the growth of the *C. perfringens* isolate but had no effect on *E. coli* colony counts. Similar growth inhibition by mesalamine was detected for *Clostridium perfringens* ATCC 13124 and *Clostridium difficile* ATCC 9689. (Data not shown.) But mesalamine did not affect the colony numbers of Lactobacillus, Enterococcus, or Bacteroides.

TABLE 1

Growth inhibition of a *Clostridium perfringens* isolate by mesalamine.
Results: (mean colony count ± SE)

| Mesalamine (mg/mL) | 0 | 3.125 | 6.25 | 12.5 | 25 | 50 | 100 |
|---|---|---|---|---|---|---|---|
| E. coli | 28.5 ± 2.3 | 29.3 ± 1.9 | 29.0 ± 2.2 | 24.0 ± 4.8 | 28.3 ± 4.6 | 33.3 ± 2.6 | 27.8 ± 2.5 |
| C. perfringens | 29.5 ± 1.3 | 38.7 ± 33.2 | 24.8 ± 13.9 | 1.0 ± 0.8* | 2.0 ± 4.0* | 1.8 ± 2.4* | 1.3 ± 2.5* |

*p, 0.0001

These results demonstrate that 5-aminosalicylates exert a selective antimicrobial action, for example on the growth of Clostridium. This selectivity of action is one of the advantages of the present invention, a feature which is useful in fighting the serious problem of clostridial infections and botulism food poisoning.

We claim:

1. A method of inhibiting the growth of a bacterial species in a human subject, comprising:
   administering to a human subject having a bacterial infection or overgrowth a pharmaceutically acceptable composition containing a 5-aminosalicylate compound in a dose effective to inhibit the growth of a bacterial species in the human subject.

2. The method of claim 1, wherein said 5-aminosalicylate compound is mesalamine, sulphasalazine, olsalazine, ipsalazine, salicylazobenzoic acid, balsalazide, or a conjugated bile acid.

3. The method of claim 1, wherein said composition is administered by a non-systemic delivery route.

4. The method of claim 3, wherein said non-systemic delivery route is a colonic delivery route.

5. The method of claim 3, wherein said non-systemic delivery route is an ingestive delivery route.

6. The method of claim 3, wherein said non-systemic delivery route is a topical application of a cream, gel, or ointment.

7. The method of claim 1, wherein said composition is administered by a systemic delivery route.

8. The method of claim 7, wherein said systemic delivery route is by ingestion, injection, intravenous drip, or implant.

9. The method of claim 7, wherein said systemic delivery route is a transdermal delivery route.

10. The method of claim 7, wherein said systemic delivery route is a transmucosal delivery route.

11. The method of claim 1, wherein said bacterial species is an obligate anaerobe.

12. The method of claim 1, wherein said bacterial species is a Clostridium species.

13. The method of claim 1, wherein said bacterial species is *Clostridium perfringens, Clostridium difficile, Clostridium tetani* or *Clostridium botulinum.*

14. A method of inhibiting the growth of a bacterial species in a human gastrointestinal tract, comprising:
administering to a human subject having a gastrointestinal bacterial infection or overgrowth a pharmaceutically acceptable composition containing a 5-aminosalicylate compound in a dose effective to inhibit the growth of a bacterial species in the gastrointestinal tract of the human subject.

15. The method of claim 14, wherein said 5-aminosalicylate compound is mesalamine, sulphasalazine, olsalazine, ipsalazine, salicylazobenzoic acid, or balsalazide.

16. The method of claim 14, wherein said 5-aminosalicylate compound is a conjugated bile acid.

17. The method of claim 16, wherein said conjugated bile acid is ursodeoxycholic acid-5-aminosalicylic acid.

18. The method of claim 14, wherein said composition is administered by a non-systemic delivery route.

19. The method of claim 18, wherein said non-systemic delivery route is a colonic delivery route.

20. The method of claim 18, wherein said non-systemic delivery route is an ingestive delivery route.

21. The method of claim 14, wherein said composition is administered by a systemic delivery route.

22. The method of claim 21, wherein said systemic delivery route is by ingestion, injection, intravenous drip, or implant.

23. The method of claim 21, wherein said systemic delivery route is a transdermal delivery route.

24. The method of claim 21, wherein said systemic delivery route is a transmucosal delivery route.

25. The method of claim 14, wherein said bacterial species is an obligate anaerobe.

26. The method of claim 14, wherein said bacterial species is a Clostridium species.

27. The method of claim 14, wherein said bacterial species is *Clostridium perfringens, Clostridium difficile, Clostridium botulinum*, or *Clostridium tetani.*

28. A method of inhibiting the growth of a bacterial species in a human gastrointestinal tract, comprising:

administering to a human subject having a gastrointestinal bacterial infection or overgrowth a pharmaceutically acceptable composition, by a colonic or ingestive delivery route, said composition comprising a 5-aminosalicylate compound selected from the group consisting of mesalamine, sulphasalazine, olsalazine, ipsalazine, salicylazobenzoic acid, balsalazide, and conjugated bile acids, in a dose effective to inhibit the growth of a bacterial species in the gastrointestinal tract of said human subject.

29. The method of claim 28, wherein said conjugated bile acid is ursodeoxycholic acid-5-aminosalicylic acid.

30. The method of claim 28, wherein said bacterial species is an obligate anaerobe.

31. The method of claim 28, wherein said bacterial species is a Clostridium species.

32. The method of claim 28, wherein said bacterial species is *Clostridium perfringens, Clostridium difficile, Clostridium botulinum*, or *Clostridium tetani.*

33. An antimicrobial pharmaceutical composition comprising a 5-aminosalicylate compound formulated in a delivery system to deliver a dose between 6.25 and 150 mg/day.

34. The antimicrobial pharmaceutical composition of claim 33, wherein said dose is between 12.5 and 150 mg/day.

35. An antimicrobial pharmaceutical composition comprising a 5-aminosalicylate compound formulated in an ingestive delivery system to deliver a dose between 6.25 and 200 mg/day.

36. The antimicrobial pharmaceutical composition of claim 35, wherein said dose is between 12.5 and 200 mg/day.

37. An antimicrobial pharmaceutical composition comprising a 5-aminosalicylate compound formulated in a delivery system to deliver a dose over 6,450 mg/day.

38. An antimicrobial pharmaceutical composition comprising a 5-aminosalicylate compound formulated in an ingestive delivery system to deliver a dose over 6,450 mg/day.

39. The antimicrobial pharmaceutical composition of any of claims 33, 35, 37, or 38, wherein said 5-aminosalicylate compound is mesalamine, sulphasalazine, olsalazine, ipsalazine, salicylazobenzoic acid, or balsalazide.

40. The antimicrobial pharmaceutical composition of any of claims 33, 35, 37, or 38, wherein said 5-aminosalicylate compound is a conjugated bile acid.

41. The antimicrobial pharmaceutical composition of claim 40, wherein said conjugated bile acid is ursodeoxycholic acid-5-aminosalicylic acid.

42. The antimicrobial pharmaceutical composition of any of claims 33 or 37, wherein said delivery system is an injection, intravenous drip, or implant delivery system.

43. The antimicrobial pharmaceutical composition of any of claims 33 or 37, wherein said delivery system is a transdermal delivery system.

44. The antimicrobial pharmaceutical composition of claim 43, wherein said delivery system comprises an adhesive patch.

45. The antimicrobial pharmaceutical composition of any of claims 33 or 37, wherein said delivery system comprises a gel or cream.

46. The antimicrobial pharmaceutical composition of any of claims 33 or 37, wherein said delivery system is a transmucosal delivery system.

47. The antimicrobial pharmaceutical composition of claim 46, wherein said delivery system is an oral transmucosal delivery system.

48. The antimicrobial pharmaceutical composition of claim 46, wherein said delivery system is a vaginal transmucosal delivery system.

49. The antimicrobial pharmaceutical composition of any of claims 33 or 37, formulated for a colonic delivery system.

50. The antimicrobial pharmaceutical composition of claim 49, wherein the colonic delivery system is an enema.

51. The antimicrobial pharmaceutical composition of claim 49, wherein the colonic delivery system is a suppository, gel, or foam.

52. The antimicrobial pharmaceutical composition of any of claims 35 or 38, wherein the ingestive delivery system is a tablet, capsule, caplet, or food additive.

53. The antimicrobial pharmaceutical composition of claim 52, wherein the ingestive delivery system comprises an enteric coating to prevent esophageal or gastric release of mesalamine.

54. The antimicrobial pharmaceutical composition of any of claims 35 or 38, wherein the ingestive delivery system comprises a lavage system.

55. The antimicrobial pharmaceutical composition of any of claims 33, 35, 37, or 38, formulated for treating a human.

56. The antimicrobial pharmaceutical composition of claim 55, formulated for pediatric use.

57. The antimicrobial pharmaceutical composition of any of claims 33, 35, 37, or 38, formulated for veterinary use.

58. The antimicrobial pharmaceutical composition of claim 57, formulated for use in a domestic or farm animal.

59. The antimicrobial pharmaceutical composition of claim 57, formulated for use in a non-human mammal or bird.

60. The antimicrobial pharmaceutical composition of claim 57, formulated for use in a non-human primate, mouse, rat, rabbit, gerbil, hamster, canine, feline, ovine, bovine, swine, pachyderm, equine, or marine mammal.

61. The antimicrobial pharmaceutical composition of claim 57, formulated for use in a duck, chicken, goose, turkey, ostrich, emu, dove, pigeon, quail, pheasant, peafowl, or guinea fowl.

62. A method of inhibiting the growth of a Clostridium species in a human subject, comprising:
administering to a human subject having a clostridial infection or overgrowth a pharmaceutically acceptable composition containing a 5-aminosalicylate compound in a dose effective to inhibit the growth of a Clostridium species in the human subject.

63. The method of claim 62, wherein said 5-aminosalicylate compound is mesalamine, sulphasalazine, olsalazine, ipsalazine, salicylazobenzoic acid, balsalazide, or a conjugated bile acid.

64. The method of claim 62, wherein said composition is administered by a non-systemic delivery route.

65. The method of claim 64, wherein said non-systemic delivery route is a colonic delivery route.

66. The method of claim 64, wherein said non-systemic delivery route is an ingestive delivery route.

67. The method of claim 64, wherein said non-systemic delivery route is a topical application of a cream, gel, or ointment.

68. The method of claim 62, wherein said composition is administered by a systemic delivery route.

69. The method of claim 68, wherein said systemic delivery route is by ingestion, injection, intravenous drip, or implant.

70. The method of claim 68, wherein said systemic delivery route is a transdermal delivery route.

71. The method of claim 68, wherein said systemic delivery route is a transmucosal delivery route.

72. The method of claim 62, wherein said Clostridium species is *Clostridium perfringens, Clostridium difficile, Clostridium tetani* or *Clostridium botulinum.*

73. A method of inhibiting the growth of a Clostridium species in a human gastrointestinal tract, comprising:
administering to a human subject having a gastrointestinal clostridial infection or overgrowth a pharmaceutically acceptable composition containing a 5-aminosalicylate compound in a dose effective to inhibit the growth of a Clostridium species in the gastrointestinal tract of the human subject.

74. The method of claim 73, wherein said 5-aminosalicylate compound is mesalamine, sulphasalazine, olsalazine, ipsalazine, salicylazobenzoic acid, or balsalazide.

75. The method of claim 73, wherein said 5-aminosalicylate compound is a conjugated bile acid.

76. The method of claim 75, wherein said conjugated bile acid is ursodeoxycholic acid-5-aminosalicylic acid.

77. The method of claim 73, wherein said composition is administered by a non-systemic delivery route.

78. The method of claim 77, wherein said non-systemic delivery route is a colonic delivery route.

79. The method of claim 78, wherein said non-systemic delivery route is an ingestive delivery route.

80. The method of claim 73, wherein said composition is administered by a systemic delivery route.

81. The method of claim 80, wherein said systemic delivery route is by ingestion, injection, intravenous drip, or implant.

82. The method of claim 80, wherein said systemic delivery route is a transdermal delivery route.

83. The method of claim 80, wherein said systemic delivery route is a transmucosal delivery route.

84. The method of claim 73, wherein said Clostridium species is *Clostridium perfringens, Clostridium difficile, Clostridium botulinum,* or *Clostridium tetani*.

* * * * *